(12) United States Patent
Ishihara et al.

(10) Patent No.: US 10,639,279 B2
(45) Date of Patent: May 5, 2020

(54) BIODEGRADABLE COMPOUND, LIPID PARTICLE, COMPOSITION CONTAINING LIPID PARTICLE, AND KIT

(71) Applicant: KABUSHIKI KAISHA TOSHIBA, Minato-ku (JP)

(72) Inventors: Mitsuko Ishihara, Setagaya (JP); Eiichi Akahoshi, Shinagawa (JP); Katsuyuki Naito, Bunkyo (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 0 days.

(21) Appl. No.: 15/918,397

(22) Filed: Mar. 12, 2018

(65) Prior Publication Data

US 2019/0076358 A1    Mar. 14, 2019

(30) Foreign Application Priority Data

Sep. 13, 2017    (JP) ................................. 2017-176055

(51) Int. Cl.

| | | |
|---|---|---|
| A61K 9/00 | (2006.01) | |
| A61K 47/64 | (2017.01) | |
| A61K 47/00 | (2006.01) | |
| C07C 69/675 | (2006.01) | |
| C07C 69/708 | (2006.01) | |
| C07C 69/732 | (2006.01) | |
| C07C 69/734 | (2006.01) | |
| C07C 229/12 | (2006.01) | |
| C07C 327/32 | (2006.01) | |
| C07D 307/16 | (2006.01) | |
| C07D 309/06 | (2006.01) | |
| C07D 309/08 | (2006.01) | |
| C07F 9/00 | (2006.01) | |
| A61K 9/127 | (2006.01) | |
| A61K 47/69 | (2017.01) | |
| C07F 9/40 | (2006.01) | |
| C12N 15/88 | (2006.01) | |

(52) U.S. Cl.
CPC ............ *A61K 9/1272* (2013.01); *A61K 47/64* (2017.08); *A61K 47/6455* (2017.08); *A61K 47/6911* (2017.08); *C07C 69/675* (2013.01); *C07C 69/708* (2013.01); *C07C 69/732* (2013.01); *C07C 69/734* (2013.01); *C07C 229/12* (2013.01); *C07C 327/32* (2013.01); *C07D 307/16* (2013.01); *C07D 309/06* (2013.01); *C07D 309/08* (2013.01); *C07F 9/00* (2013.01); *C07F 9/4006* (2013.01); *C07F 9/4075* (2013.01); *C12N 15/88* (2013.01); *A61K 9/127* (2013.01); *A61K 9/1275* (2013.01)

(58) Field of Classification Search
CPC ...... A61K 9/1272; A61K 9/00; A61K 9/1278; A61K 47/6911; A61K 47/64; A61K 47/00; C07C 69/675; C07C 69/708; C07C 69/732; C07C 69/734; C07C 229/12; C07C 327/32; C07D 307/16; C07D 309/06; C07D 309/08; C07F 9/00; C07F 9/4006; C07F 9/4075

See application file for complete search history.

(56) References Cited

U.S. PATENT DOCUMENTS

| | | | |
|---|---|---|---|
| 4,959,465 A | * | 9/1990 | Klemann ................ A23L 33/26 426/611 |
| 5,534,499 A | | 7/1996 | Ansell |
| 5,820,873 A | | 10/1998 | Choi et al. |
| 5,885,613 A | | 3/1999 | Holland et al. |
| 6,320,017 B1 | | 11/2001 | Ansell |
| 9,012,498 B2 | | 4/2015 | Manoharan et al. |
| 2006/0051405 A1 | | 3/2006 | MacLachlan et al. |
| 2010/0015218 A1 | | 1/2010 | Jadhav et al. |
| 2011/0091525 A1 | | 4/2011 | Heyes et al. |
| 2017/0326103 A1 | | 11/2017 | Porter et al. |

FOREIGN PATENT DOCUMENTS

| | | | |
|---|---|---|---|
| JP | 2000/353310 | * | 12/2000 |
| JP | 3920330 | | 5/2007 |
| JP | 2010-519203 | | 6/2010 |
| JP | 5893611 | | 3/2016 |
| WO | WO 2005/026372 A1 | | 3/2005 |
| WO | WO 2006/007712 A1 | | 1/2006 |
| WO | WO 2016/023082 A1 | | 2/2016 |

OTHER PUBLICATIONS

Martin A Maier, et al. "Biodegradable Lipids Enabling Rapidly Eliminated Lipid Nanoparticles for Systemic Delivery of RNAi Therapeutics", Molecular Therapy, vol. 21, No. 8, 2013, 9 pages.

Lalanne, M. et al., "Synthesis and biological evaluation of two glycerolipidic prodrugs of didanosine for direct lymphatic delivery against HIV" Bioorganic and Medicinal Chemistry Letters, vol. 17, 2007, pp. 2237-2240.

* cited by examiner

*Primary Examiner* — Timothy R Rozof

(74) *Attorney, Agent, or Firm* — Oblon, McClelland, Maier & Neustadt, L.L.P.

(57) ABSTRACT

The compound according to the present embodiment is represented by the following formula (1):

$$\text{Q-L-CHR}_2 \qquad (1)$$

wherein,

Q is a non-cationic aliphatic group that does not contain nitrogen but contains oxy;

L is a single bond or an aliphatic group containing no nitrogen; Rs are $C_{12}$-$C_{24}$ aliphatic group, the same or different; and at least one R contains, in the main chain or side chain thereof, a linking group $L^R$ selected from the group consisting of —C(=O)—O—, —O—C(=O)—, —O—C(=O)—O—, —S—C(=O)—, —C(=O)—S—, —C(=O)—NH—, and —NH—C(=O)—).

48 Claims, 2 Drawing Sheets

BIODEGRADABLE COMPOUND, LIPID PARTICLE, COMPOSITION CONTAINING LIPID PARTICLE, AND KIT

CROSS REFERENCE TO RELATED APPLICATIONS

This application is based upon and claims the benefit of priority from the prior Japanese Patent Application No. 2017-176055, filed on Sep. 13, 2017, the entire contents of which are incorporated herein by reference.

FIELD

The present embodiment relates to a biodegradable compound having an intracellularly degradable structure and a lipid particle containing the same. The present embodiment also relates to a composition and a kit which contain the lipid particle and are used to deliver an active agent such as a nucleic acid.

BACKGROUND

Liposomes have been studied for the purposes of treating various diseases. Liposomes are valuable materials for delivering a therapeutic drug or an active agent to a selected target site in vivo because they are microcapsules constituted of lipid and having a particle size on the order of nanometers, can encapsulate various compounds and the like in the microcapsule, and have excellent biocompatibility and the like. For such a purpose, large unilamellar vesicle liposomes (LUV) having an average particle size of 100 nm or more are generally used, and various materials have been developed as materials constituting such a membrane.

Such a liposome can be constituted of one type of lipid. As the lipid in such a case, for example, a phospholipid having a head and a hydrophobic tail bound thereto is used, and these lipids associate to form a membrane, which constitutes a microcapsule capable of encapsulating an active agent and the like. In order to add the remarkable characteristics to a liposome, however, a lipid mixture for constituting a liposome is generally used. The lipid mixture contains a mixture of: a lipid having excellent biodegradability; a lipid for suppressing the aggregation of liposome to be formed; a lipid having an effect of suppressing the leakage of the encapsulated matter; a lipid having an effect of membrane fusion; and the like.

Each lipid has been studied in order to enhance the characteristics of a liposome. For example, a medical liposome dedicated to gene transfer preferably satisfies high biodegradability, high biocompatibility, high ability to transfect an active agent, and low cytotoxicity, and then lipids that can constitute such a liposome are desired.

Various compounds have been developed as such lipids, but there is a great diversity in the state of an organism which the compounds are applied to and in diseases to be treated. It is desirable to have more types of lipids among which to select in accordance with these conditions. Furthermore, there is a demand for lipids that can constitute a liposome having characteristics surpassing those of conventional liposomes.

Against the above-mentioned problems, the present embodiment is to provide: a novel compound as a lipid capable of constituting a liposome; and a lipid particle for which the compound is used; and a composition and a kit.

DETAILED DESCRIPTION

Figure 1:
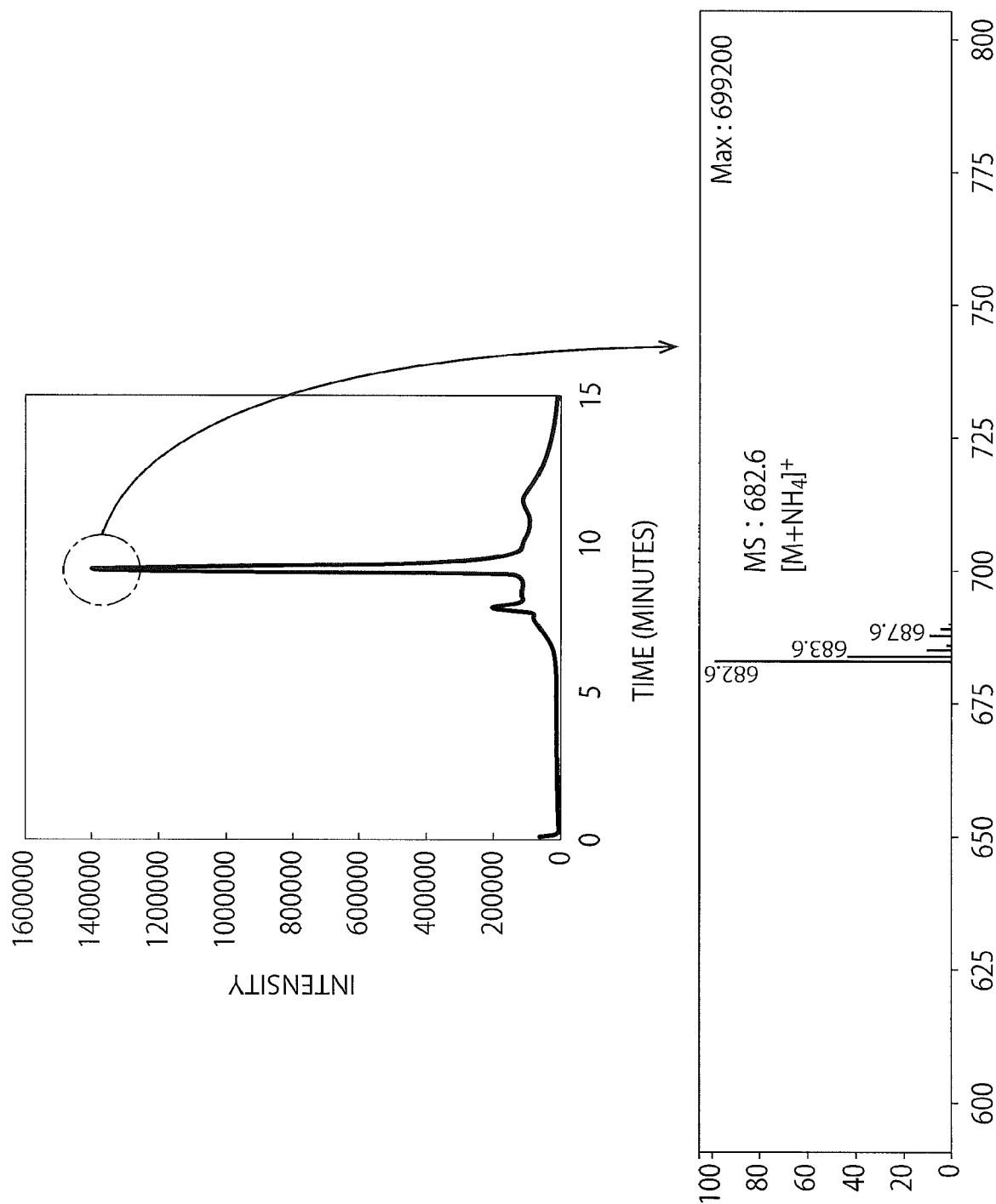
FIG. 1 is a chart depicting the measurement results of high performance liquid chromatography of the compound in Example 1.

Embodiments will now be explained with reference to the accompanying drawings.

The compound according to the present embodiment is represented by the following formula (1):

$$Q\text{-}L\text{-}CHR_2 \qquad (1)$$

(wherein,

Q is a non-cationic aliphatic group that does not contain nitrogen but contains oxy;

L is a single bond or an aliphatic group containing no nitrogen; Rs are $C_{12}$-$C_{24}$ aliphatic groups, the same or different; and at least one R contains, in the main chain or side chain thereof, a linking group $L^R$ selected from the group consisting of —C(=O)—O—, —O—C(=O)—, —O—C(=O)—O—, —S—C(=O)—, —C(=O)—S—, —C(=O)—NH—, and —NH—C(=O)—).

In addition, the lipid particle according to the embodiment is characterized by containing the above-mentioned compound.

In addition, the composition according to the embodiment is characterized by containing the above-mentioned lipid particle and a carrier.

In addition, the kit according to the embodiment contains the above-mentioned lipid particle and a composition containing an incorporation agent for incorporating the lipid particle into a cell.

Definition

In the present embodiment, a value range indicated using "to" include both endpoints, unless otherwise particularly limited, and the unit thereof is the same. For example, 10 to 25 mol % means 10 mol % or more and 25 mol % or less.

In the present embodiment, the expressions, "$C_x$-$C_y$", "$C_x$", and the like mean the number of carbon atoms in a molecule or a substituent. For example, $C_1$-$C_6$ alkyl means an alkyl having one or more but six or less carbon atoms. In addition, in the present embodiment, halogenated alkyl refers to an alkyl one or more hydrogen atoms of which have been substituted with a halogen such as fluorine, and, for example, fluoroaryl refers to an aryl group one or more hydrogen atoms of which have been substituted with fluorine.

In the present embodiment, unless otherwise particularly limited, alkyl means a monovalent group resulting from an alkane in which a hydrogen atom has been removed from any carbon atom. In addition, the term, "alkyl" encompasses straight-chain and branched-chain alkyls. Furthermore, cycloalkyl means an alkyl containing a cyclic structure. Cycloalkyl also refers to a cyclic structure in which there has been substitution with a straight-chain or branched-chain alkyl.

Next, alkenyl means a monovalent group resulting from an alkene in which a hydrogen atom has been removed from any carbon atom.

Next, a hydrocarbon group means a monovalent, bivalent, or multivalent group containing carbon, hydrogen, and optionally oxygen or nitrogen. Then, an aliphatic group is a hydrocarbon group not containing an aromatic ring, and may take any of a linear, a branched-chain, and a cyclic structure and may be a combination thereof. In addition, unless otherwise particularly limited, an aliphatic group may contain an unsaturated bond. Furthermore, unless otherwise particularly limited, an aliphatic group may contain a hetero atom such as nitrogen, oxygen, sulfur, selenium, fluorine, chlorine, or bromine. In addition, an aliphatic group may be monovalent, bivalent, or multivalent. In addition, an aromatic hydrocarbon group contains an aromatic ring and optionally has an aliphatic hydrocarbon group as a substituent.

Biodegradable Lipid Compound

The compound according to the embodiment is a suitable compound as a lipid constituting a liposome. The compound has a biodegradable group at the hydrophobic portion thereof and functions as a biodegradable lipid compound. The compound contains no cationic group at the head thereof, and is characterized by suppressing the bonding of proteins in a cell when applied to an organism and thus having low toxicity. In addition, when a liposome constituted of this lipid compound, the surface of the liposome is non-cationic, and hence the liposome has lower toxicity to a cell and affords a higher transfection rate of an active agent such as a nucleic acid.

Such a lipid compound is represented by the following general formula (1). Hereinafter, Q and R in the formula may be referred to as a head and a hydrophobic group respectively.

Q-L-CHR$_2$ (1)

(wherein,
Q is a non-cationic aliphatic group that does not contain nitrogen but contains oxy;
L is a single bond or an aliphatic group containing no nitrogen; Rs are C$_{12}$-C$_{24}$ aliphatic groups, the same or different; and at least one R contains, in the main chain or side chain thereof, a linking group L$^R$ selected from the group consisting of —C(=O)—O—, —O—C(=O)—, —O—C(=O)—O—, —S—C(=O)—, —C(=O)—S—, —C(=O)—NH—, and —NH—C(=O)—).

One characteristic of the compound according to the embodiment is that the head thereof has no cationic group. Q can contain an anionic group, but is preferably a neutral group containing no polar group. Q needs to contain no nitrogen atom because nitrogen atoms often constitute cationic groups.

L is a linking group that binds the head Q to —CHR$_2$ containing two hydrophobic groups. This linking group may be a single bond or an aliphatic group. However, this linking group needs to contain no nitrogen.

In addition, when L is an aliphatic group, the structure thereof preferably has an ester structure.

On the basis of having such a structure, the compound represented by the general formula (1) is easily prepared, for example, by effecting an ester reaction between a compound containing the head structure and a compound containing the hydrophobic group portion. Such an ester structure is formed by reaction between an acid radical such as a carboxylic acid, a carboxylic acid chloride, a phosphoric acid, or a thiocarboxylic acid and a hydroxy or mercapto compound such as an alcohol or a thiol.

Specifically, L preferably contains an ester structure selected from the group consisting of —C(=O)—O—, —O—C(=O)—, —O—C(=O)—O—, —C(=S)—O—, —O—C(=S)—, —O—C(=S)—O—, —S—C(=O)—, —C(=O)—S—, and —O—P(=O)OR'—O— (wherein R' is hydrogen, a non-cationic aliphatic group, or —CHR$_2$). Here, because a phosphoric acid is a polybasic acid, the compound can have a plurality of the Q heads or a plurality of structures equal to —CHR$_2$ of the general formula (1). Among these ester structures, an ester structure selected from the group consisting of —O—C(=O)—O— and —O—C(=O)—O— is particularly preferable.

When L is an aliphatic group and contains an ester structure, L is preferably represented by the following general formula (1A):

L$^A_a$-L$^O$-L$^A_a$- (1A)

(wherein,
L$^A$ is alkylene or cycloalkylene that is optionally substituted independently with oxygen;
L$^O$ is an ester structure selected from the group consisting of —C(=O)—O—, —O—C(=O)—, —O—C(=O)—O—, —S—C(=O)—, and —C(=O)—S—, and a is independently a number from 0 to 6). Here, the number of carbon atoms contained in L$^A$ is not limited to any particular one, but the total number of carbon atoms contained in two L$^A$s is preferably from 1 to 6.

In addition, Q contains oxy. Oxy means a bivalent linking group, —O—. However, —O— in an ester structure contained in the above-mentioned L is not included in oxy structures in the present embodiment. In other words, when Q contains, for example, a carboxylato group, —(=O)—O—, Q contains an oxy structure other than the —O— contained therein.

In the compound according to the embodiment, an oxy structure is contained in a hydroxy, an alkoxy, a halogenated oxy, an ether, an alkylene oxy structure, and the like. In addition, the compound may contain a plurality of oxy structures.

A preferable example of Q can be represented by the following general formula (1B-1).

Q$^O$-[(CH$_2$)$_{b1}$—O—]$_{b2}$— (1B-1)

(wherein,
Q$^O$ is hydrogen, halogen, alkyl, or alkenyl;
b1 is a number from 0 to 3;
b2 is a number from 1 to 3; and
the total number of carbon atoms contained in the formula (1B) is 6 or less.)

Here, alkyl is preferably C$_1$-C$_3$ alkyl, and alkenyl is preferably C$_2$-C$_3$ alkenyl.

In addition, Q preferably contains an oxy structure as a cyclic ether structure. Specifically, a preferable example of Q can be represented by the following general formula (1B-2).

Q$^1$-L$^B$ (1B-2)

(wherein,
Q$^1$ is a cyclo ether; and
L$^B$ is alkylene.)

Here, a cyclo ether is preferably C$_3$-C$_6$.

The compound according to the embodiment has —CHR$_2$ bound to the head. Here, R represents a hydrophobic group, and two Rs may be the same or different. The hydrophobic group generally contain a relatively long hydrocarbon chain.

In addition, the hydrophobic group contains a linking group containing a carboxylato group and the like in part thereof, specifically a linking group selected from the group consisting of —C(=O)—O—, —O—C(=O)—O—, —O—C(=O)—O—, —S—C(=O)—, —C(=O)—S—, —C(=O)—NH—, and —NH—C(=O)—. These linking groups function as biodegradable groups when the compound according to the embodiment is used for liposomes.

A preferable example of the hydrophobic group R can be represented by the following formula (1C).

-L$^{C1}$-C(=O)—O-L$^{C2}$ (1C)

(wherein,
L$^{C1}$ is alkylene; and
L$^{C2}$ is alkenyl.)

L$^{C1}$ and L$^{C2}$ may have a branched-chain structure or a cyclic structure, preferably has a fewer side chains when having a branched-chain structure, and most preferably has a straight-chain structure.

More specifically, L$^{C1}$ and L$^{C2}$ are preferably represented by the following formulae (1C-1) and (1C-2) respectively.

—(CH$_2$)$_{c1}$— (1C-1)

—CH$_2$—CH=CH—(CH$_2$)$_{c2}$—H (1C-2)

(wherein,
c1 is a number from 1 to 10; and
c2 is a number from 1 to 10.)

Here, for the hydrophobic group to achieve sufficient hydrophobicity, c1 is preferably a number from 4 to 8, and the longest molecular chain contained in the hydrophobic group R preferably has 8 atoms or more.

Each moiety of the compound according to the embodiment has such a structure as above-mentioned, and the compound according to the embodiment preferably has a structure represented by the following formulae (1-01) to (1-20).

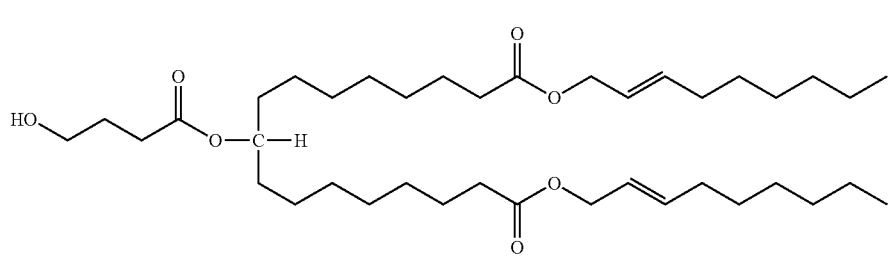

(1-01)

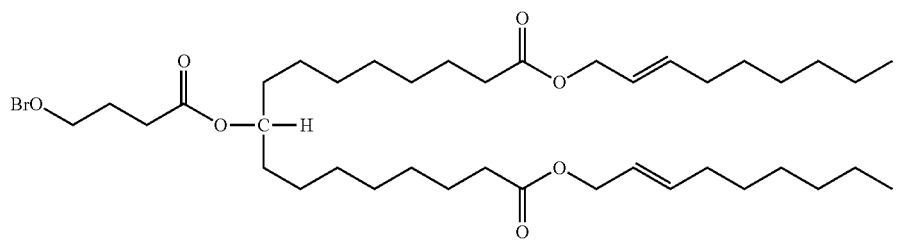

(1-02)

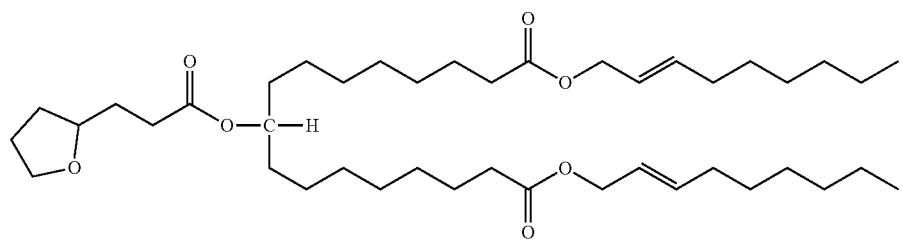

(1-03)

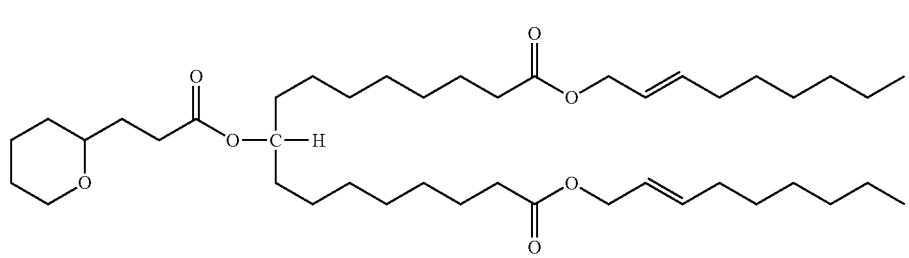

(1-04)

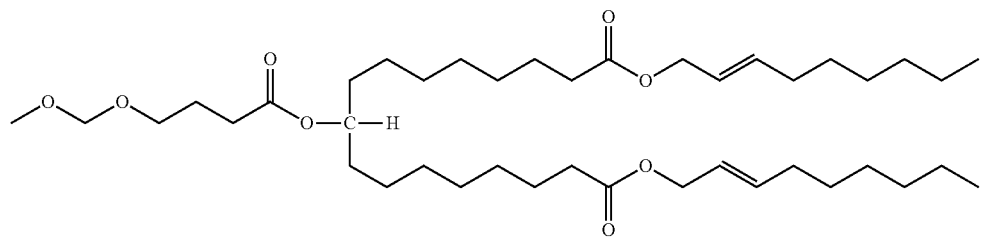
(1-05)
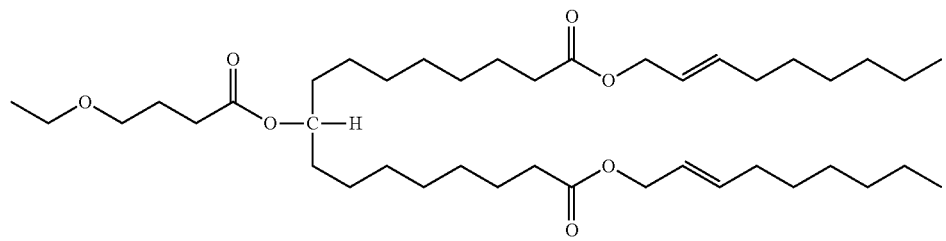
(1-06)
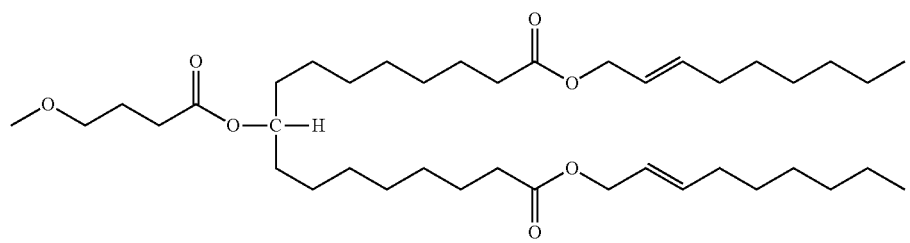
(1-07)
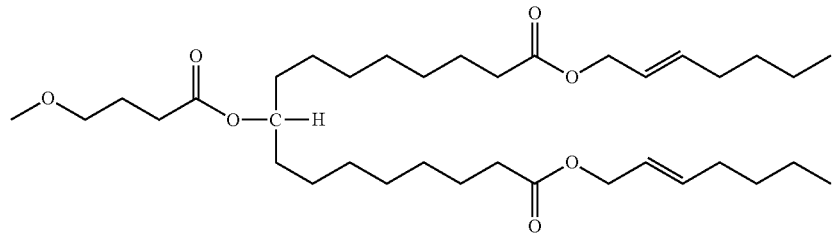
(1-08)
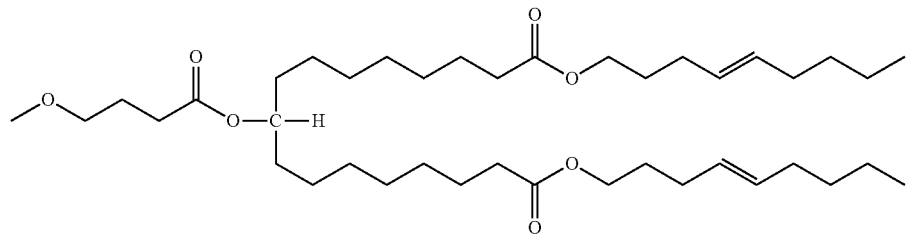
(1-09)
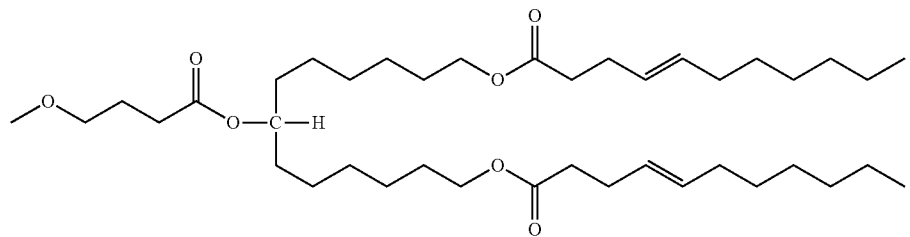
(1-10)

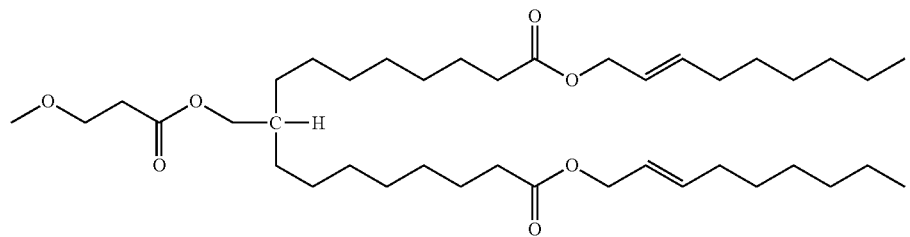
(1-11)
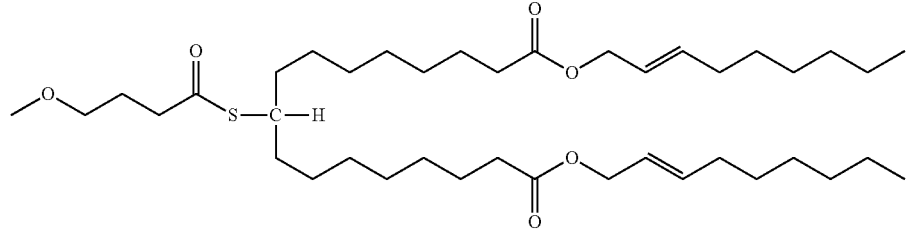
(1-12)
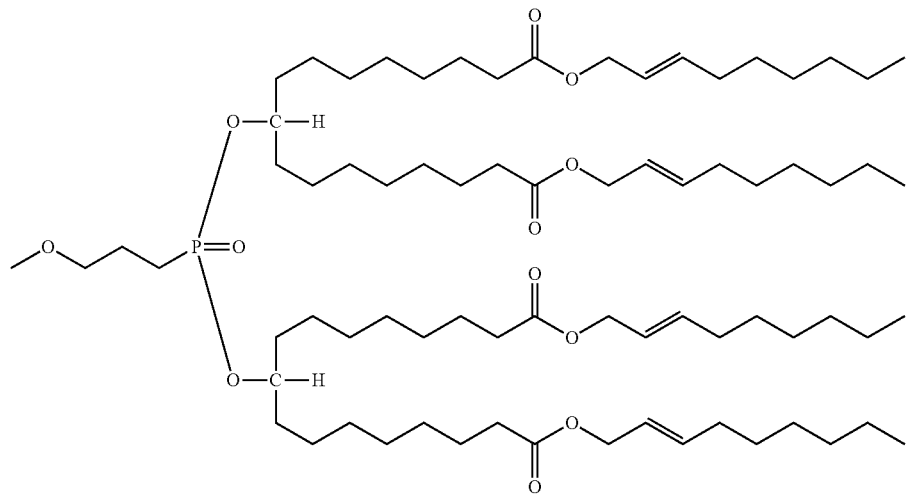
(1-13)
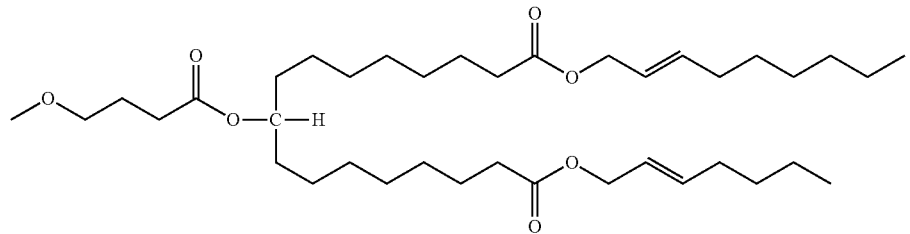
(1-14)
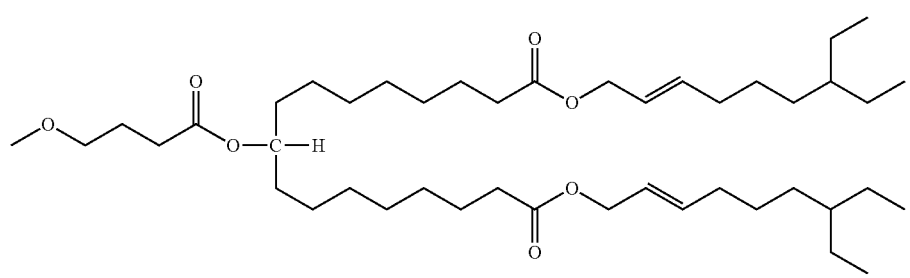
(1-15)

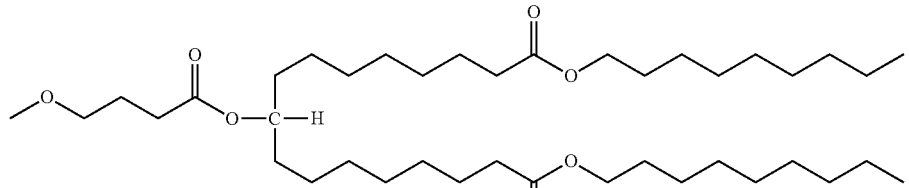
(1-16)
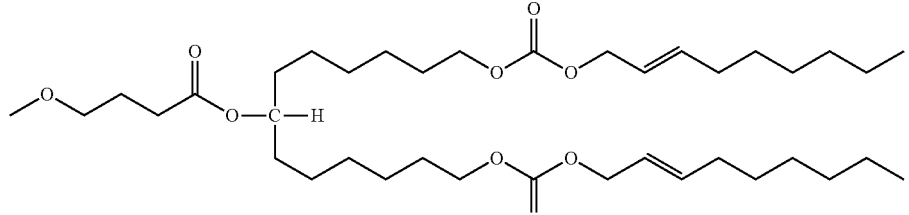
(1-17)
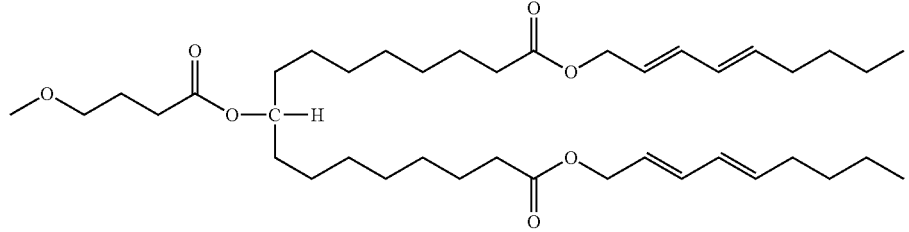
(1-18)
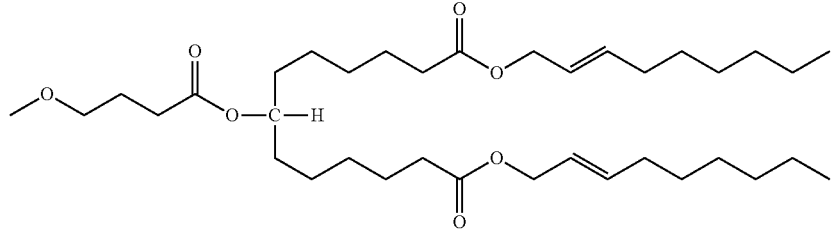
(1-19)
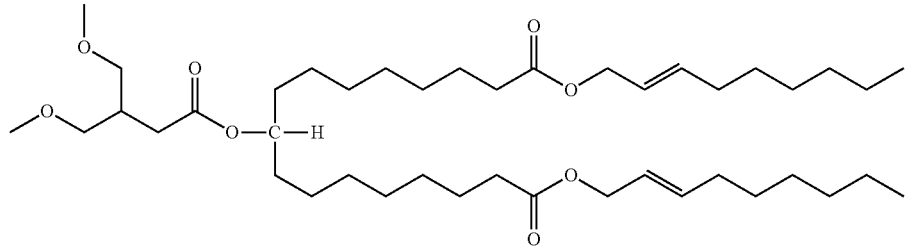
(1-20)
Among these, (1-01) to (1-07) are particularly preferable because the compounds can achieve excellent characteristics when used for liposomes.
Method of Producing Compound
Such a compound can be produced in accordance with, for example, the following process chart.
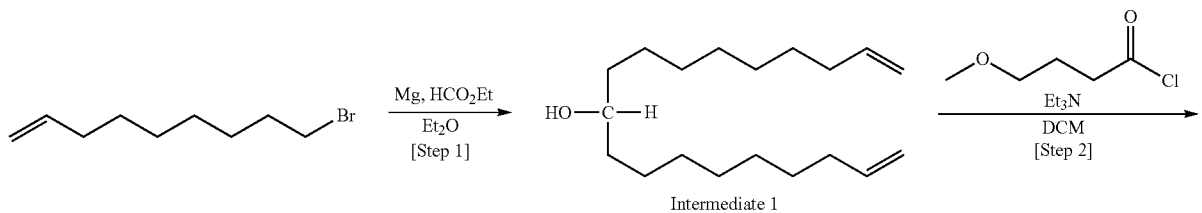
Intermediate 1

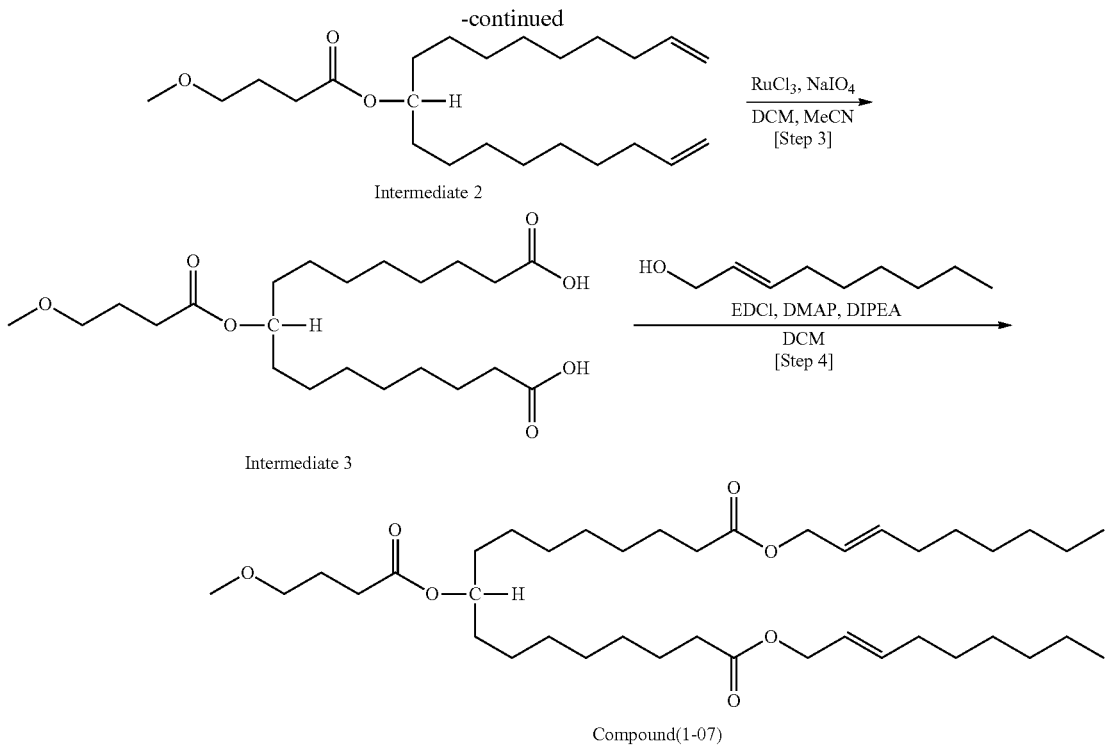

Such a method of synthesizing a compound has a fewer steps compared to a conventionally known process of synthesizing a lipid compound, and enables more efficient production.

Lipid Particle

According to the embodiment, a lipid particle is provided. A typical example of this lipid particle is a liposome, but is not limited thereto, and other examples include a lipoplex which is a complex formed of a liposome and a nucleic acid or the like. In addition, the liposome may be either a unilamellar vesicle or a multilamellar vesicle.

The lipid particle according to the embodiment contains the compound represented by the above-mentioned formula (1). In addition, desirably the lipid particle further contains a membrane-forming lipid and an aggregation-reducing lipid.

The compound represented by the above-mentioned formula (1) also functions as a membrane-forming lipid, but, in the embodiment, the "membrane-forming lipid" is not to encompass the compound represented by the formula (1)

As a membrane-forming lipid, any lipid can be used as long as it is a lipid generally used for liposomes. This lipid is preferably a lipid having excellent biodegradability.

Specific examples of such membrane-forming lipids include diacylphosphatidylcholine, diacylphosphatidyl ethanol amine, ceramide, sphingomyelin, dihydrosphingomyelin, kephalin, cerebroside, and the like. The membrane-forming lipids used for lipid particles in the embodiment are suitably selected considering the size of a liposome of interest, the in vivo stability of a liposome, and the like. Among these, diacylphosphatidylcholine and diacylphosphatidyl ethanol amine are preferable. In this regard, the hydrocarbon chain of an acyl group contained in the lipid preferably has a length of 10 to 20. This hydrocarbon chain may be a saturated hydrocarbon group or an unsaturated hydrocarbon group.

As such membrane-forming lipids, various ones are known, and preferable examples include:
1,2-dioleoyl-sn-glycero-3-phosphoethanol amine (DOPE),
1,2-stearoyl-sn-glycero-3-phosphoethanol amine (DSPE),
1,2-dipalmitoyl-sn-glycero-3-phosphatidylcholine (DPPC),
1-palmitoyl-2-oleoyl-sn-glycero-3-phosphatidylcholine (POPC),
1,2-di-O-octadecyl-3-trimethylammonium propane (DOTMA),
1,2-dioleoyl-3-dimethylammonium propane (DODAP),
1,2-dimyristoyl-3-di methylammonium propane (14:0 DAP),
1,2-dipalmitoyl-3-dimethylammonium propane (16:0 DAP),
1,2-distearoyl-3-dimethylammonium propane (18:0 DAP),
N-(4-carboxybenzyl)-N,N-dimethyl-2,3-bis(oleoyloxy)propane (DOBAQ),
1,2-dioleoyl-3-trimethylammonium propane (DOTAP),
1,2-dioleoyl-sn-glycero-3-phosphochlorine (DOPC),
1,2-dilinoleoyl-sn-glycero-3-phosphochlorine (DLPC),
1,2-dioleoyl-sn-glycero-3-phospho-L-serine (DOPS), cholesterol, and the like. These can achieve a membrane fusion effect in addition to the function of forming a membrane such as a liposome.

The aggregation-reducing lipid used in the embodiment effects the function of covering aggregation inhibition between particles in the formulation of lipid particles. As such a lipid, various ones are known, and any lipid can be selected for use for lipid particles according to the embodiment. Examples of such lipids include polyethylene glycol (PEG)-modified lipids, polyamide oligomers derived from omega-amino(oligoethylene glycol)alkane acid monomers (U.S. Pat. No. 6,320,017), monosialoganglioside, and the like. More specifically, ATTA lipids such as ATTA8-DPSE described in U.S. Pat. No. 6,320,017 and polyethylene glycol lipid conjugates described in U.S. Pat. Nos. 5,820,873, 5,534,499, and 5,885,613 can be used.

PEG-modified lipids can form anchoring lipid parts on the surface of lipid particles when the lipid particles have been formed. Examples of such PEG-modified lipids include PEG-modified phosphatidyl ethanol amine, PEG-modified phosphatidic acid, PEG-ceramide conjugate (for example, C14 PEG-Cer or C20 PEG-Cer described in Japan Patent No. 3920330), PEG-modified dialkylamine, PEG-modified 1,2-diacyloxypropane-3-amine, PEG-modified diacyl glycerol (for example, 1,2-d imyristoyl-sn-g lycerol-methoxypolyethylene glycol; PEG-DMG), and PEG-modified dialkylglycerol. Among these, PEG-modified diacyl glycerol and PEG-modified dialkylglycerol are preferable.

When a bulky modified group such as PEG is bound to the lipid surface, the bonding between the modified group and a lipid particle affects the stability of the lipid particle or the liposome. For example, U.S. Pat. No. 5,820,873 indicates that characteristics such as the length of an acyl chain in a PEG-modified lipid, the degree of saturation of an acyl chain, and the size of a steric hindrance head group affect the stability of a lipid particle. Thus, adjusting these characteristics enables lipid particles of interest to be obtained. For example, shortened modified groups in a PEG-modified lipid enable lipid particles to be broken more quickly, and lengthened modified groups can prolong residence time in blood plasma.

As a result, the delivery of lipid particles to a target tissue may be improved.

The lipid particle can further contain other lipids. As such other lipids, any lipid that is selected from those generally used in lipid particles can be used. For example, a lipid having relatively low cytotoxicity can be used in combination in order to adjust cytotoxicity. In addition, in order to incorporate a functional group for binding a ligand to a lipid particle, a lipid having a specific structure can be used in combination.

Furthermore, in using the lipid particle as a liposome, the lipid particle can contain sterol, for example, cholesterol, as a lipid for suppressing the leakage of the encapsulated matter. Furthermore, a substance acting on a target can be coupled with the lipid particle. As a coupling method in such a case, any conventionally known method can be adopted.

The lipid particle is constituted of these lipids in combination but is not to be limited thereto because the blending ratios of the lipids constituting the lipid particle are adjusted in accordance with the purpose. However, on the basis of the total number of moles of lipids used in the lipid particle, 25 to 75 mol % of the lipid compound represented by the formula (1),
25 to 75 mol % of a membrane-forming lipid, and
1 to 10 mol % of an aggregation-reducing lipid are generally blended, and,
25 to 50 mol % of the lipid compound represented by the formula (1);
47.5 to 72.5 mol % of a membrane-forming lipid; and
1 to 10 mol %, for example, 2.5 mol %, of an aggregation-reducing lipid;

are preferable. Here, it is important to achieve a balance between the compound of the formula (1) and the membrane-forming lipid, and the presence of only one of them will not afford a sufficiently high transfection rate of an active agent. Thus, the blended ratio of the compound of the formula (1) to the membrane-forming lipid is preferably 1:0.5 to 1:3, more preferably 1:1 to 1:2, on the basis of the number of moles.

The lipid particle according to the embodiment can further contain an active agent. In the embodiment, an active agent refers to a substance capable of achieving a specific effect on a cell, tissue, organ, or analyte.

Such a specific effect may be any effect which is biological, physiological, or cosmetic. The use of the lipid particle according to the embodiment enables various active agents to be delivered to an in vivo site of interest. The active agents may be encapsulated in the lipid particle, bound to the external or internal lipid surface, or disposed inside the lipid layer.

A typical example of an active agent is a nucleic acid, and examples thereof include a nucleic acid selected from the group consisting of plasmids, oligonucleotides, polynucleotides, small interfering RNAs (siRNAs), micro RNAs (miRNAs), DNAs, aptamers, and ribozymes. In addition, antisense oligonucleotides, antagomirs, aDNAs, plasmids, ribosome RNAs (rRNAs), transfer RNAs (tRNAs), small nuclear RNAs (snRNAs), mRNAs, and the like can also be used.

As a miRNA, a miRNA in which 17 to 25 nucleotide units are linked can be used. In a more preferred embodiment, the nucleic acid is an oligonucleotide in which 15 to 50 or 20 to 30 nucleotide units are linked. siRNA contains, for example, 16 to 30 nucleotide units and can have a double-stranded region. In another embodiment, the nucleic acid is an immunostimulatory oligonucleotide, a decoy oligonucleotide, a supermir, a miRNA mimic, or a miRNA inhibitor. A supermir refers to a single-stranded, double-stranded or partially double-stranded oligomer or polymer of RNA or deoxyribonucleic acid DNA or both or modifications thereof, which has a nucleotide sequence that is substantially identical to a miRNA and that is antisense with respect to its target. miRNA mimics represent a class of molecules that can be used to imitate the gene silencing ability of one or more miRNAs. The term "miRNA mimic" refers to synthetic non-coding RNAs (i.e. the miRNA is not obtained by purification from a source of the endogenous miRNA) that are capable of entering the RNAi pathway and regulating gene expression.

The nucleic acid used in combination with a lipid particle is limited to no particular form. The nucleic acid can, for example, be single-stranded DNA or RNA, or double-stranded DNA or RNA, or DNA-RNA hybrids. Examples of double-stranded RNA include siRNA. Examples of single-stranded nucleic acids include antisense oligonucleotides, ribozymes, miRNA, and triplex-forming oligonucleotides.

When the lipid particle according to the embodiment contains a nucleic acid, it can further contain a compound that will be bound to a nucleic acid. Examples of such compounds include basic proteins and basic peptides, and preferable examples include protamines, histones, and salts thereof. For example, histones and salts thereof have properties of binding to a nucleic acid and enfolding the nucleic acid molecules. Protamines have properties of binding to a nucleic acid and then winding the nucleic acid. Thus, these compounds are effective for encapsulating a nucleic acid into a lipid particle.

In addition, the lipid particle according to the embodiment can further contain a compound that regulates the expression of a nucleic acid in a cell. This is preferable because regulating the expression of a nucleic acid in a cell can achieve the effects of visualizing and killing the cell to which a liposome has been delivered. Examples of such compounds include retinoic acids, cyclic adenosine monophosphates (cAMP), ascorbic acids, and the like.

The lipid particle according to the embodiment may contain lipoproteins, apolipoproteins, and the like.

As active agents, other therapeutic agents can be used. Specific examples of usable therapeutic agents include peptides, polypeptides, cytokines, growth factors, apoptotic factors, differentiation-inducing factors, cell surface receptors and ligands thereof, hormones, and the like. More specifically, examples of therapeutic agents include anti-inflammatory compounds, antidepressants, stimulants, analgesics, antibiotics, birth control medication, antipyretics, vasodilators, anti-angiogenics, cellular vasoactive agents (cytovascular agents), signal transduction inhibitors, cardiovascular agents, oncology drugs, hormones, and steroids.

When the lipid particle is used in combination with an active agent, the active agent is preferably incorporated into cells at a higher transfection rate. In addition, cell death by cytotoxicity that depends on the characteristics of the lipid is preferably low. In cases where a nucleic acid is transfected using a conventionally known lipid particle, the transfection rate is generally low, and the ratio of cell death by cytotoxicity is high. On the contrary, the use of the lipid particle according to the embodiment can afford a high transfection rate of a nucleic acid and reduce cell death. Specifically, the transfection rate by a conventional lipid particle is about 10% and the rate of cell death by electroporation is 60 to 70%, whereas, for the lipid particle according to the embodiment, those are represented to 70% or more and 30% or less respectively.

The lipid particle according to the embodiment can be formed to any size in accordance with the purpose. However, in using the lipid particle according to the embodiment for medicinal use, the lipid particle generally has a size on the order of nanometers. Specifically, the lipid particle according to the embodiment has an average particle size of generally 50 nm to 300 nm, preferably 50 nm to 200 nm. The size of the lipid particle can be adjusted by any method. For example, the lipid particle can be made smaller by ultrasonication. In addition, the lipid particle size can be adjusted by allowing lipid particles to permeate a polycarbonate membrane or a ceramic membrane and thus separating them. In this regard, in the embodiment, the average particle size of the lipid particle can be measured with, for example, a Zetasizer based on dynamic light scattering.

The lipid particle according to the embodiment has an in vivo half-life ($t_{1/2}$) of generally less than 3 hours, preferably less than 2 hours, particularly preferably less than 1 hour. Here, the in vivo half-life means a half-life in the liver, spleen, or blood plasma, for example. In the embodiment, the compound of the formula (1) constituting a lipid has a biodegradable group, and thus the lipid has a half-life of, for example, less than 10% of a lipid particle made of a lipid containing no biodegradable group.

Method of Producing Lipid Particle

The lipid particle according to the embodiment can be produced by any conventionally known method. As a method of producing lipid particles and liposomes, the Bangham method, an organic solvent extraction method, a surfactant removal method, a freezing and thawing method, and the like are known, and they can also be adopted. Alternatively, a lipid particle can be formed spontaneously, for example, by introducing the compound represented by the formula (1), further introducing a membrane-forming lipid and an aggregation-reducing lipid into an organic solvent such as alcohol, and then adding an aqueous buffer to the resulting mixture. This combination of an aqueous buffer and an active agent enables an active agent to be transfected into the lipid particle.

The lipid particle according to the embodiment can be used to delivery an active agent to a cell.

In particular, the delivery of an active agent such as a nucleic acid to a cell is used in all fields such as genetic engineering, production of recombination proteins, and medical technologies known as gene therapy and cytology.

Composition

The lipid particle according to the embodiment can be used as a composition. For example, a composition containing the lipid particle according to the embodiment and a carrier is provided. Such a composition can be applied to medicinal uses.

As a carrier, any carrier that is selected from those conventionally known can be used, and examples thereof include water, a saline solution such as a physiological saline solution, a glycine aqueous solution, a buffer, and the like. Further in addition to these carriers, a glycoprotein such as albumin, lipoprotein, apolipoprotein, or globulin can be used in combination for the purpose of improving stability or other purposes.

The composition according to the embodiment can be prepared by a standard method. As a carrier, a physiological saline solution is generally used. For a composition containing a saline solution or another salt-containing carrier, a carrier is preferably added after the lipid particle is formed. Accordingly, in general, the lipid particle and an active agent such as a nucleic acid are combined, and then the composition is diluted with a pharmaceutically acceptable carrier such as physiological saline.

The composition according to the embodiment may contain an adjunct if necessary. For example, in medicinal use, the pharmaceutical composition can contain a pharmaceutically acceptable adjunct such as a pH adjustor, a buffer agent, or a tonicity adjustor as an adjunct so that the composition can become closer to the physiological condition. Examples of adjuncts achieving such a function include sodium acetate, sodium lactate, sodium chloride, potassium chloride, calcium chloride, and the like. The composition according to the embodiment can also contain a lipid protective agent for improving storage stability. Examples of such protective agents include: lipotrophic free radical quenchers such as α-tocopherol which suppress damage caused by free radicals; and water-soluble chelators such as ferrioxamine which suppress overacidic damage caused to a lipid.

Other than these, the above-mentioned active agents or the like can be added to the composition. These active agents may be the same as or different from the active agents use in combination with the lipid particle. To the composition, a compound that binds to a nucleic acid or a compound that adjusts the expression of a nucleic acid can also be added.

The concentration of the lipid particle contained in the composition according to the embodiment is not limited to any particular value, and the content of the lipid particle in the composition is generally 0.01 to 30 mass %, preferably 0.05 to 10 mass %. The concentration of the lipid particle can suitably be selected in accordance with the purpose.

The composition according to the embodiment can be sterilized by a conventionally known method. A sterilized composition not only can be packaged as an as-is administerable preparation, but also can be packaged in dried form. Combining the dried composition with an aqueous sterile solution immediately before administration allows the composition to be used as an administerable preparation.

The composition according to the embodiment can be formed in kit form. The kit according to the embodiment includes the above-mentioned lipid particle and an incorporation agent for incorporating the lipid particle into a cell, and can do so in any form. Examples of kits include: a kit of separate containers holding a dispersion in which a lipid particle containing no active agent is dispersed in a carrier, and an active agent respectively; a kit of separate containers holding a dried lipid particle, an active agent, and a carrier respectively; and the like. Furthermore, the dried lipid particle or lipid particle dispersion and an active agent can also be treated as separate articles so that users can select each article in accordance with the purpose.

The kit can be used in combination with a reagent used in transfecting a nucleic acid.

Method of Utilizing Pharmaceutical Composition

When the lipid particle according to the embodiment is used for medicinal use, the composition can be used to treat various diseases in humans or animals. Treatment is made possible by delivering a therapeutic agent to a cell of interest, in which the therapeutic agent is applied as an active agent used in combination with the lipid particle.

For example, it is possible to prevent or treat a disease by delivering a kind of nucleic acid to a cell so that they can come in contact. Examples of such nucleic acids include oligonucleotides, siRNAs, plasmids, antisenses, or ribozymes. In addition, nucleic acids can be delivered either in vitro or in vivo.

For in vivo administration of the pharmaceutical composition, parenteral administration, i.e., intraarticular administration, intravenous administration, intra peritoneal administration, subcutaneous administration, or intramuscular administration is preferably adopted. The intravenous administration or intraperitoneal administration of the pharmaceutical composition can also be carried out by bolus injection In addition, the pharmaceutical preparation according to the embodiment can be directly applied to a target tissue so that the pharmaceutical composition can be brought in contact with the target tissue. Administration into meninge or the like by dripping and administration with an endoscope are also possible.

In a particular embodiment, the pharmaceutical composition is generally treated at a physiologic temperature (about 37° C.) in a period of 1 to 24 hours, preferably 2 to 8 hours. A subject cell for in vitro application is not limited to any particular one. For example, the cell may be a vertebrate cell, invertebrate cell, or plant cell. In a preferred embodiment, however, the cell is an animal cell, more preferably a mammalian cell, most preferably a human cell.

EXAMPLES

[Example 1] Synthesis of Compound (1-07)

The compound (1-07) was synthesized in accordance with the above-mentioned production process. Specifically, the procedures were carried out in the following manner.

Magnesium (3.48 g, 142.99 mmol, 4.4 eq.), diethyl ether (25 mL), and iodine (1 mg) were fed into a 100 mL four-neck flask under an argon atmosphere. To this, 9-bromonone-1-ene (20.00 g, 97.49 mmol, 3 eq.) was added dropwise under reflux. The resulting mixture was allowed to react for one hour, and the obtained Grignard reagent together with diethyl ether (32.8 mL) was transferred to a dropping funnel. The Grignard reagent was added dropwise, at 0° C. or less over one hour, into a 200 mL four-neck flask in which ethyl formate (2.41 g, 32.49 mmol, 1 eq.) and diethyl ether (32.8 mL) had been fed. After the resulting mixture was allowed to react at room temperature for one hour, acetone (20 mL) was added, and water (40 mL) and a 10% $H_2SO_4$ aqueous solution (53 mL) were sequentially added for partition. The aqueous layer was further extracted twice using diethyl ether (50 mL), and all combined organic layers were dried over $NaSO_4$. The crude product (18.33 g) obtained by filtration concentration was purified by column chromatography (silica gel: 200 g). As a developing solution, hexane was used first, and then a liquid mixture of ethyl acetate and hexane (2% ethyl acetate) was used. As a result, 7.43 g of an intermediate 1, a white solid, was obtained (81% yield) (the step 1).

Under an argon atmosphere, the intermediate 1 (5.00 g, 17.80 mmol, 1 eq.) and dichloromethane (DCM, 50 mL) were fed into a 200 mL four-neck flask and dissolved, and triethylamine (3.63 g, 35.6 mmol, 2 eq.) was further added. At 0° C., 4-methoxybutyryl chloride (4.86 g, 35.6 mmol, 2 eq.) was added dropwise. The resulting mixture was stirred overnight; the reaction solution was added to water (400 mL) for partition; and then the organic layer was washed with a saturated $NaHCO_3$ solution (400 mL) and a saturated saline solution (100 mL) and dried over $Na_2SO_4$. The crude product (19.3 g) obtained by filtration concentration was purified by column chromatography (silica gel: 200 g, developing solution: liquid mixture of ethyl acetate and hexane (2% ethyl acetate)) to obtain 6.43 g (95% yield) of an intermediate 2, a colorless and transparent oil (the step 2).

In a 500 mL four-neck flask, the intermediate 2 (6.1 g, 16.03 mmol, 1 eq.) was added and dissolved in dichloromethane (120 mL) and acetonitrile (120 mL), and then ruthenium chloride (III) (414.9 mg, 0.989 mmol, Ru=40%) was added. Sodium periodate (34.28 g, 160.3 mmol, 10 eq.) dissolved in water (180 mL) was added dropwise at 10° C. or less and stirred at 10° C. overnight. After the completion of reaction, water (30 mL) was added to the reaction solution for partition. A saturated saline solution (100 mL) was added to the organic layer, and a 3% $Na_2S$ aqueous solution was added dropwise until the color changed. Until the resulting solution became acidic, 1 M HCl was added thereto for partition.

The crude product (7.8 g) obtained by drying the organic layer over $Na_2SO_4$ and concentrating the layer by filtration was purified by column chromatography (silica gel: 100 g). As a developing solution, chloroform was used first, and then a liquid mixture of methanol and chloroform (10% methanol) was used. As a result, 4.32 g of an intermediate 3, a brown oil, was obtained (64% yield) (the step 3).

In a 200 mL four-neck flask, the intermediate 3 (2.0 g, 4.8 mmol, 1 eq.) was dissolved in dichloromethane (100 mL); and cis-2-nonane-1-ol (1.6 g, 11.7 mmol, 2.44 eq.), 4-dimethylaminopyridine (DMAP, 58 mg, 0.48 mmol, 0.1 eq.), N,N-diisopropylethylamine (DIPEA, 3 g, 23.5 mmol, 4.9 eq.), and 1-(3-dimethylaminopropyl)-3-ethylcarbodiimide hydrochloride (EDCl, 22.5 g, 11.7 mmol, 2.44 eq.) were added; and the resulting mixture was stirred at room temperature overnight. The reaction solution was washed with water (100 mL), a saturated $NaHCO_3$ solution (100 mL), and a saturated saline solution (100 mL) in turn, and the organic layer was dried over $Na_2SO_4$. The crude product (3.8 g) obtained by filtration concentration was purified by column chromatography (silica gel: 50 g, developing solution: liquid mixture of methanol and chloroform (10% methanol)). As a result, 300 mg of the compound (1-07), a slightly yellow oil, was obtained (9% yield) (the step 4).

Then, the obtained compound (1-07) was analyzed by high performance liquid chromatography.

The analysis was carried out using a high performance liquid chromatograph mass spectrometer (Agilent 1100 Series, made by Agilent Technologies Japan, Ltd.). For liquid chromatography, 100% methanol was used as the mobile phase A, and 10 mM ammonium acetate was used as the mobile phase B; and for the column, silica C8 was used. Electrospraying was selected for ionization in the mass spectrometry, and a quadrupole was used for ion separation. The compound (1-07) was dissolved in methanol to make a 5 µg/mL solution, which was injected in an amount of 1.0 µL at a flow rate of 0.2 mL/min. On the basis of the molecular weight calculated from the formula (1-07), measurements were taken with a detectable ion mass range set to 600 to 900, so that the main peak was detected at an m/z (mass/charge ratio) of 682.6. This m/z ratio agreed with the m/z ratio of the ion of the compound of the formula (1-07) to which an ammonium ion were bound. No other noticeable peaks were detected. The obtained results are as shown in FIG. 1. The results have confirmed that the compound obtained by synthesis was one represented by the formula (1-07).

[Example 2] Making of Liposome

A plasmid solution and a peptide were used to make a core composite. As a plasmid, a plasmid (pAmp-CMV-NLuc) with cytomegalovirus early promoter/enhancer, NLuc gene, IRES, simian virus 40 large T antigen gene, transcription terminator and origin of simian virus 40 replication was used. As a peptide, protamine derived from salmon was used. Into a microtube, 100 µL of a peptide solution (0.24 mg/mL, 10 mM HEPES, pH 5.4) was dispensed. While being stirred with a vortex mixer (1,500 rpm), the dispensed peptide solution was mixed with 200 µL of a plasmid solution (0.15 mg/mL, 10 mM HEPES, pH 5.4) added dropwise, to make a core composite.

The liposome for encapsulating the core composite was adjusted by an ethanol injection method. The liposome was labelled with a rhodamine fluorescent dye-linked lipid (Rhod-PE) to measure cell uptake rates with FACS. Into a microtube, 50 µL of a lipid solution was dispensed. As the lipid solution, a solution of the compound represented by the below-mentioned formula (R-01), DOPE, cholesterol, DMG-PEG, and Rhod-PE at 5:4:3:0.3:0.1 by mole (Comparative Example 1A), or a solution of the compound of the formula (1-07), DOPE, cholesterol, DMG-PEG, and Rhod-PE at 5:4:3:0.3:0.1 by mole (Example 1A) was used.

The obtained liposome was measured for the amount of DNA encapsulated. The measurement was taken using the Quant-iT PicoGreen dsDNA Assay Kit (Thermo Fisher Scientific Inc.). To 95 µL of a Tris-EDTA buffer containing 0.1% Triton-X100 (tradename), 5.0 µL of the liposome solution was added, and gently suspended. The resulting solution was allowed to stand at room temperature for 30 minutes, and 100 µL of a PicoGreen solution diluted 200-fold with a Tris-EDTA buffer was added to the solution and mixed well. The resulting solution was allowed to stand at room temperature for five minutes, and then measured for fluorescence intensity (excitation wavelength: 485 nm, fluorescent wavelength: 530 nm) using a micro-titer plate reader, Mithras LB-940 (tradename, from Berthold Japan Co., Ltd).

Figure 2:
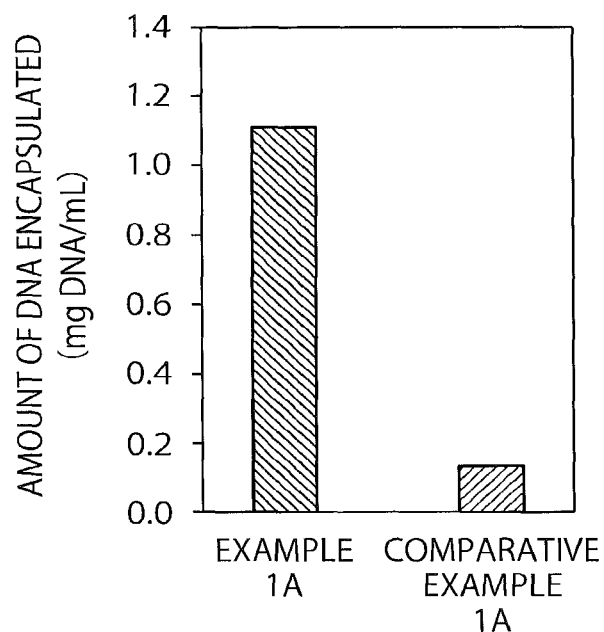
FIG. 2 is a graph depicting the amounts of DNA encapsulated in the liposomes in Example 1A and Comparative Example 1A.

The concentration of DNA was determined using a calibration curve made with a λ DNA having a known concentration. From the obtained value, the amount of DNA encapsulated in the liposome was calculated as the amount of DNA per 1 mL of solution (µg DNA/mL). The results are shown in FIG. 2. The results have revealed that the liposome containing the compound of the formula (1-07) has a higher amount of encapsulated DNA than the liposome containing the compound of the formula (R-01).

Next, rates of liposome uptaken into cells were measured.

Liposome uptake rates were measured by FACS (fluorescence activated cell sorting) using a flow cytometer (FACSVerse, made by BD Biosciences). As the cell, a human T-cell leukemia cell: Jurkat (purchased from ATCC) was used. In a 4-well dish (from Matsunami), 200 µL of a 1×10$^6$ cells/mL cell suspension was seeded, and then 10 µL of a rhodamine-labelled liposome solution was added. After the addition, the cells were cultured in a 5% $CO_2$ atmosphere at 37° C. in an incubator for 48 hours, and the cells were collected together with the medium. From the cell suspension, the cells were collected by centrifugation (200×g, 5 min., 4° C.). (using a high-speed refrigerated micro centrifuge, MX-307, made by Tomy Seiko Co., Ltd.), and then the cells were suspended in 500 µL of a phosphate buffered physiological saline containing 1% bovine serum albumin to prepare a specimen for FACS. The frequency distribution of the rhodamine fluorescent cell contained in this specimen was measured by FACS, and the uptake rates of the liposome

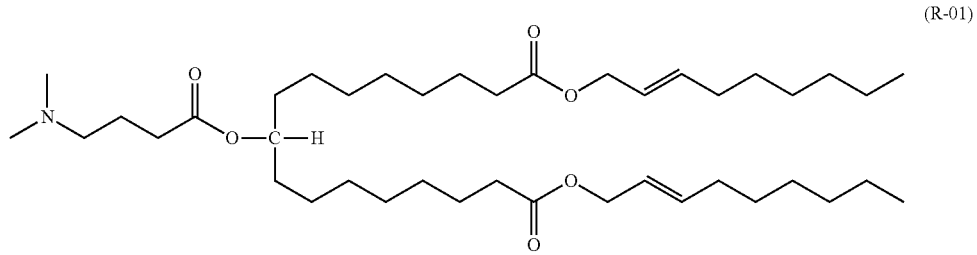 [SMILES: CCCCCC/C=C/COC(=O)CCCCCCCC(CCCCCCCC(=O)OC/C=C/CCCCCC)OC(=O)CCCN(C)C]

(R-01)

Figure 3:
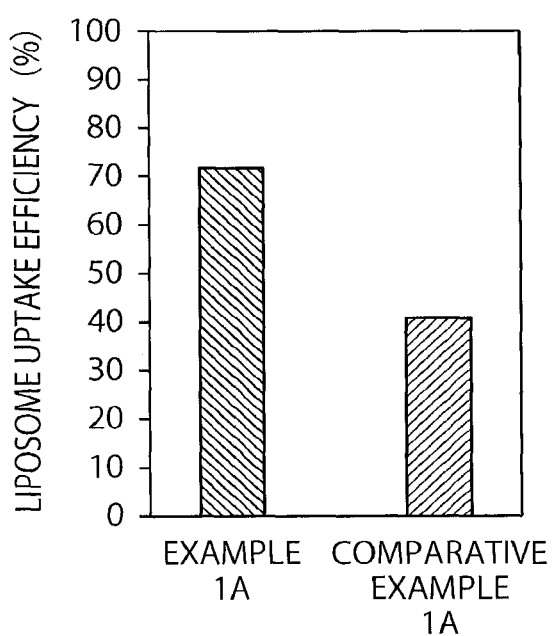
FIG. 3 is a graph depicting the uptake amounts of the liposomes in Example 1A and Comparative Example 1A.

While being stirred with a vortex mixer (1,500 rpm), the dispensed lipid solution was mixed with 50 µL of the core composite added dropwise. After the dropwise addition, 400 µL of 10 mM HEPES (pH 5.4) was gently added to the resulting solution to prepare liposome. To the resulting solution, 400 µL of 10 mM HEPES (pH 5.4) was further added and gently mixed, followed by buffer exchange and concentration using an ultrafiltration spin column (PT-1014, made by APRO Science Inc.), to make 100 µL of liposome (10 mM HEPES, pH 7.3).

into the cell were calculated. The results are shown in FIG. 3. The results have revealed that the liposome containing the compound of the formula (1-07) has a higher uptake rate of liposome into cells than the liposome containing the compound of the formula (R-01).

[Example 3] Comparison in the Transfection Rate of Nucleic Acid into Cell

The transfection rate of DNA in the liposome into cells was evaluated by using FACS to measure the amount of GFP expressed when pCMV-EGFP, a plasmid vector (pDNA) that expresses GFP, was transfected into a cell. As the cell, a primary normal human mammary cell (HMEC: LIFELINE product, available from Kurabo Industries Ltd.) was used. The cells were seeded in a 24-well plate at $5 \times 10^4$ cells/well, and after 24 hours, 0.5 µg of pDNA was added to each well for transfection. As a conventional lipid particle, a lipid particle containing a cationic lipid having polyamide amine dendron as a polar group was used and added at 12.5 µL per well. For electroporation, a poration pulse of 150V for 10 ms and a driving pulse of 10V for 50 ms were applied five times. The liposome for which the lipid according to the embodiment (1-07) was used was added at 10 µL per well.

After 48 hours, the cells were collected, and the proportion of cells that emitted the fluorescence based on the expression of GFP was determined by FACS. After the cells collected after 48 hours were PI-stained, the cell survival rate was calculated from the proportion of dead cells that emitted the fluorescence based on PI by FACS.

TABLE 1

|  | Liposome Using Conventional Lipid | Electroporation | Liposome Using Lipid according to Embodiment |
|---|---|---|---|
| Transfection Rate (%) | 10.9 | 30.1 | 94.0 |
| Survival Rate (%) | 71.1 | 55.9 | 99.5 |

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the invention.

The invention claimed is:

1. A compound represented by the following formula (1):

Q-L-CHR$_2$    (1)

wherein,
Q is a non-cationic aliphatic group which is represented by the following formula (1B-1):

$Q^0$-[(CH$_2$)$_{b1}$—O—]$_{b2}$-    (1B-1)

wherein
$Q^0$ is hydrogen, halogen, alkyl, or alkenyl;
b1 is a number from 0 to 3;
b2 is a number from 1 to 3; and
the total number of carbon atoms contained in the formula (1B-1) is 6 or less;
L is an aliphatic group which is represented by the following formula (1A):

-L$^A_a$-L$^0$-L$^A_a$-    (1A)

wherein
L$^A$ is alkylene or cycloalkylene that is optionally substituted independently with oxygen;
L$^0$ is an ester structure selected from the group consisting of —C(=O)—O—, —O—C(=O)—, —O—C(=O)—O—, —S—C(=O)—, and —C(=O)—S—, and a is independently a number from 0 to 6);
Rs are C$_{12}$-C$_{24}$ aliphatic groups, the same or different; and at least one R contains, in the main chain or side chain thereof, a linking group L$^R$ selected from the group consisting of —C(=O)—O—, —O—C(=O)—, —O—C(=O)—O—, —S—C(=O)—, —C(=O)—S—, —C(=O)—NH—, and —NH—C(=O)—.

2. The compound according to claim 1, wherein the L contains an ester structure selected from the group consisting of —C(=O)—O—, —O—C(=O)—, —O—C(=O)—O—, —C(=S)—O—, —O—C(=S)—, —O—C(=S)—O—, —S—C(=O)—, and —C(=O) S—.

3. The compound according to claim 1, wherein the Q is represented by the following formula (1B-2):

$Q^1$-L$^B$-    (1B-2)

wherein,
$Q^1$ is a cyclo ether; and
L$^B$ is alkylene.

4. The compound according to claim 1, wherein the at least one R is represented by the following formula (1C):

-L$^{C1}$-C(=O)—O-L$^{C2}$    (1C)

wherein,
L$^{C1}$ is alkylene; and
L$^{C2}$ is alkenyl.

5. The compound according to claim 4, wherein the L$^{C1}$ and the L$^{C2}$ are represented by the following formulae (1C-1) and (1C-2) respectively:

—(CH$_2$)$_{c1}$-    (1C-1)

—CH$_2$—CH=CH—(CH$_2$)$_{c2}$—H(1C-2)

wherein
c1 is a number from 1 to 10; and
c2 is a number from 1 to 10.

6. The compound according to claim 5, wherein the c1 is a number from 4 to 8.

7. The compound according to claim 1, wherein the longest molecular chain contained in the R has 8 or more atoms.

8. The compound according to claim 1, wherein is said compound is a compound presented by one of the following formulae (1-01), (1-02), (1-05) to (1-12), and (1-14) to (1-20)

(1-01)

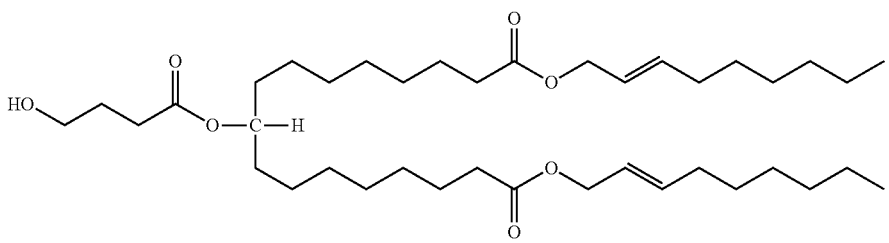

(1-02)
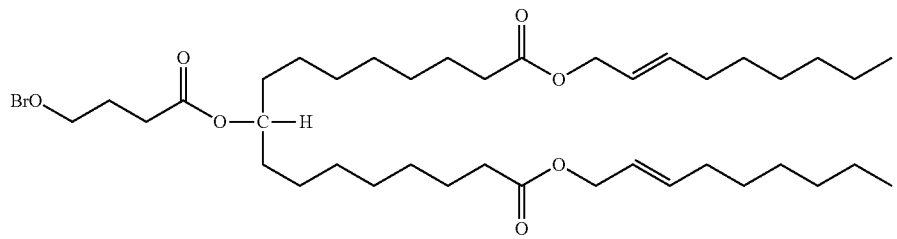
(1-05)
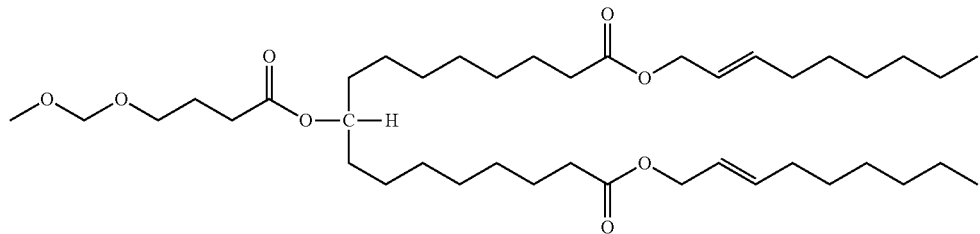
(1-06)
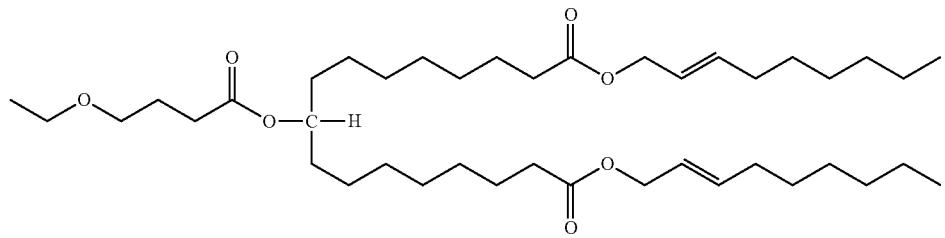
(1-07)
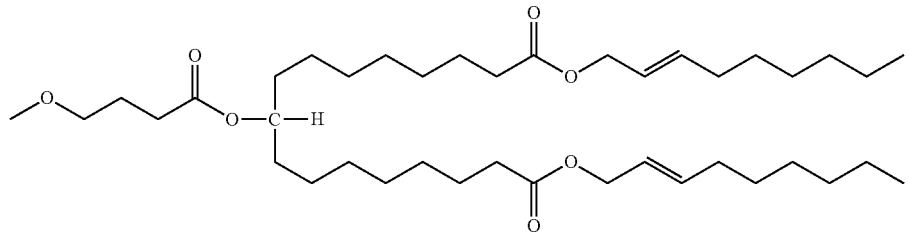
(1-08)
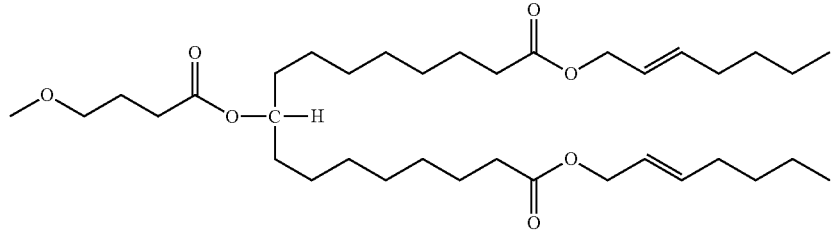
(1-09)
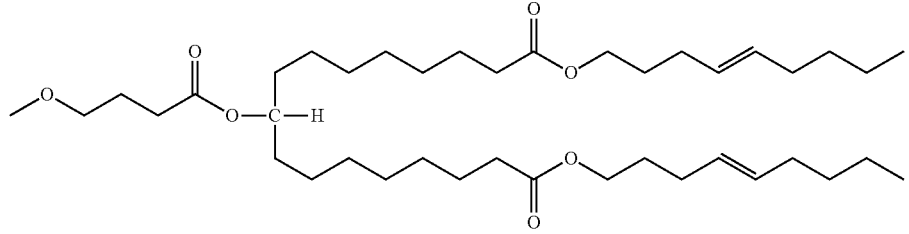

-continued
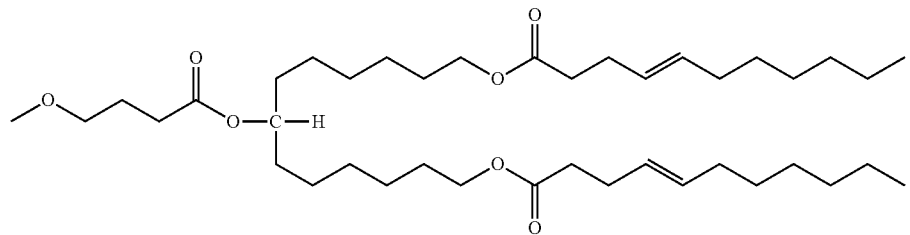
(1-10)
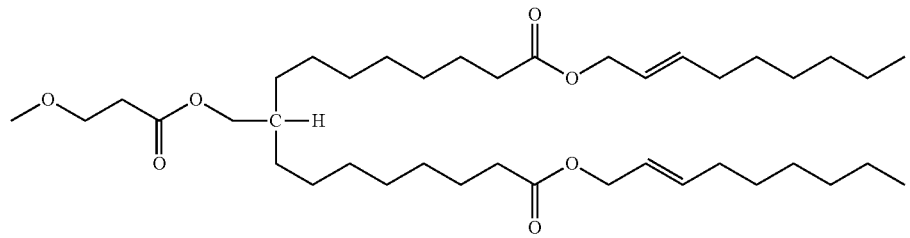
(1-11)
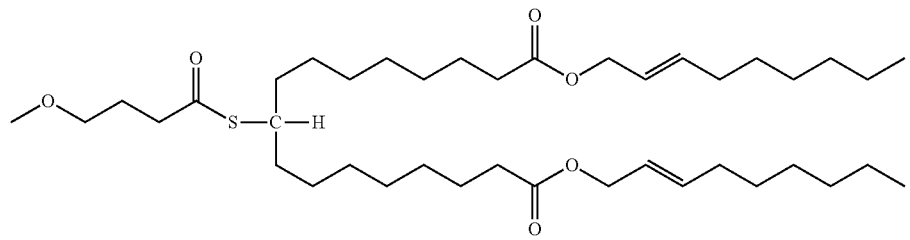
(1-12)
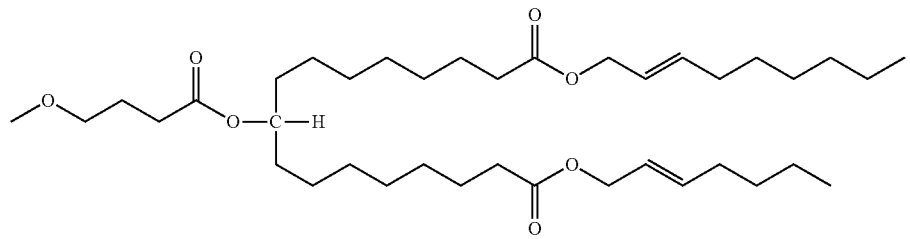
(1-14)
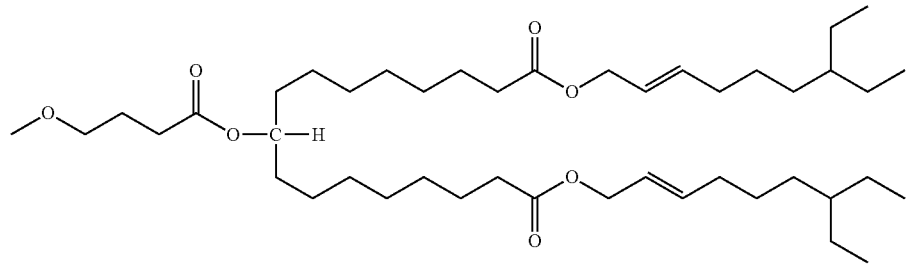
(1-15)
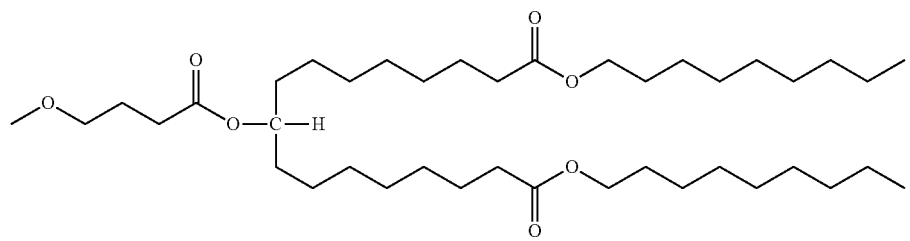
(1-16)

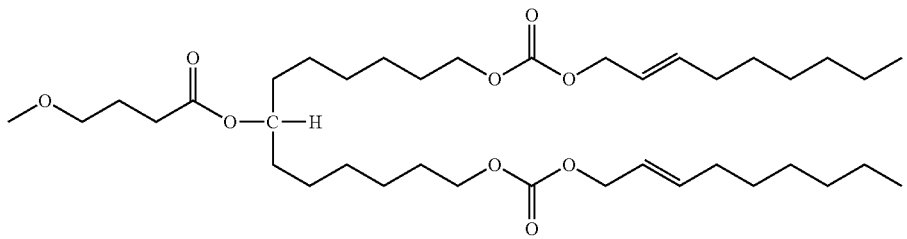

(1-17)

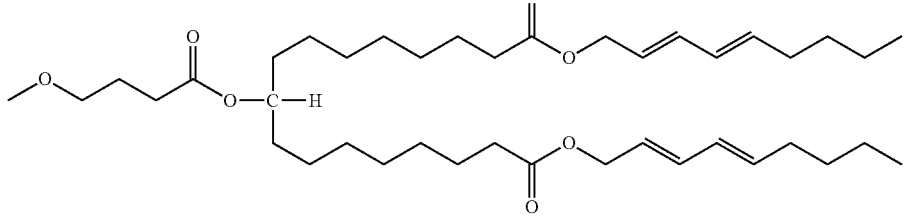

(1-18)

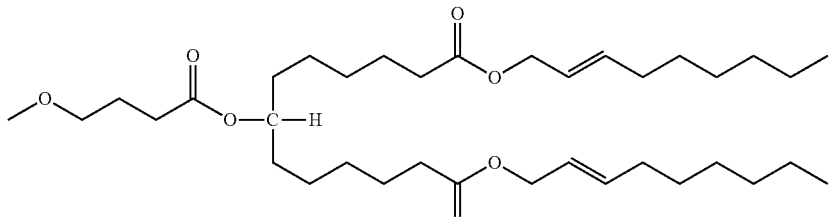

(1-19)

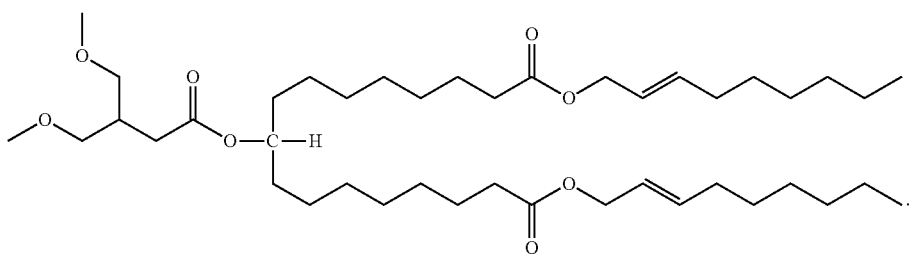

(1-20)

9. A lipid particle comprising the compound according to claim 1.

10. The lipid particle according to claim 9, further comprising a membrane-forming lipid and an aggregation-reducing lipid.

11. The lipid particle according to claim 10, wherein the membrane-forming lipid is selected from the group consisting of
1,2-dioleoyl-sn-glycero-3-phosphoethanol amine (DOPE),
1,2-stearoyl-sn-glycero-3-phosphoethanol amine (DSPE),
1,2-dipalmitoyl-sn-glycero-3-phosphatidylcholine (DPPC),
1-palmitoyl-2-oleoyl-sn-glycero-3-phosphatidylcholine (POPC),
1,2-di-O-octadecyl-3-trimethylammonium propane (DOTMA),
1,2-dioleoyl-3-dimethylammonium propane (DODAP),
1,2-dimyristoyl-3-di methylammonium propane (14:0 DAP),
1,2-dipalmitoyl-3-dimethylammonium propane (16:0 DAP),
1,2-distearoyl-3-dimethylammonium propane (18:0 DAP),
N-(4-carboxybenzyl)-N,N-dimethyl-2,3-bis(oleoyloxy) propane (DOBAQ),
1,2-dioleoyl-3-trimethylammonium propane (DOTAP),
1,2-dioleoyl-sn-glycero-3-phosphochlorine (DOPC),
1,2-dilinoleoyl-sn-glycero-3-phosphochlorine (DLPC),
1,2-dioleoyl-sn-glycero-3-phospho-L-serine (DOPS),
cholesterol, and the like; and
wherein the aggregation-reducing lipid is a polyethylene glycol (PEG)-modified lipid.

12. The lipid particle according to claim 9, further comprising an active agent.

13. The lipid particle according to claim 12, wherein the active agent is a nucleic acid selected from the group consisting of plasmids, oligonucleotides, polynucleotides, siRNAs, micro RNAs, DNAs, aptamers, and ribozymes.

14. The lipid particle according to claim 13, further comprising a compound that binds to a nucleic acid.

15. The lipid particle according to claim 14, wherein the compound that binds to a nucleic acid is a basic protein or a basic peptide.

16. The lipid particle according to claim 14, wherein the compound that binds to a nucleic acid is a protamine or a histone.

17. The lipid particle according to claim 14, further comprising a compound that regulates the expression of a nucleic acid in a cell.

18. A composition comprising the lipid particle according to claim 9 and a carrier.

19. A kit comprising the lipid particle according to claim 9 and a composition containing an incorporation agent for incorporating the lipid particle into a cell.

20. A compound represented by the following formula (1):

$$Q\text{-}L\text{-}CHR_2 \qquad (1)$$

wherein,

Q is a non-cationic aliphatic group that does not contain nitrogen but contains oxy;

L is a single bond or an aliphatic group containing no nitrogen;

Rs are $C_{12}$-$C_{24}$ aliphatic groups, the same or different; and at least one R is represented by the following formula (1C):

$$-(CH_2)_{c1}-C(=O)-O-CH_2-CH=CH-(CH_2)_{c2}-H \qquad (1C)$$

wherein, c1 is a number from 1 to 10; and c2 is a number from 1 to 10.

21. The compound according to claim 20, wherein the L contains an ester structure selected from the group consisting of —C(=O)—O—, —O—C(=O)—, —O—C(=O)—O—, —C(=S)—O—, —O—C(=S)—, —O—C(=S)—O—, —S—C(=O)—, and —C(=O) S—.

22. The compound according to claim 20, wherein the L is represented by the following formula (1A):

$$-L^A_a\text{-}L^O\text{-}L^A_a\text{-} \qquad (1A)$$

wherein $L^A$ is alkylene or cycloalkylene that is optionally substituted independently with oxygen;

$L^O$ is an ester structure selected from the group consisting of —C(=O)—O—, —O—C(=O)—, —O—C(=O)—O—, —S—C(=O)—, and —C(=O)—S—, and a is independently a number from 0 to 6.

23. The compound according to claim 22, wherein the Q is represented by the following formula (1B-1):

$$Q^0\text{-}[(CH_2)_{b1}-O-]_{b2}\text{-} \qquad (1B\text{-}1)$$

wherein $Q^0$ is hydrogen, halogen, alkyl, or alkenyl;

b1 is a number from 0 to 3;

b2 is a number from 1 to 3; and the total number of carbon atoms contained in the formula (1B-1) is 6 or less.

24. The compound according to claim 22, wherein the Q is represented by the following formula (1B-2):

$$Q^1\text{-}L^B\text{-} \qquad (1B\text{-}2)$$

wherein, $Q^1$ is a cyclo ether; and $L^B$ is alkylene.

25. The compound according to claim 20, wherein the c1 is a number from 4 to 8.

26. The compound according to claim 20, wherein the longest molecular chain contained in the R has 8 or more atoms.

27. The compound according to claim 20, wherein said compound is a compound presented by one of the following formulae (1-01) to (1-12) and (1-14) to (1-20)

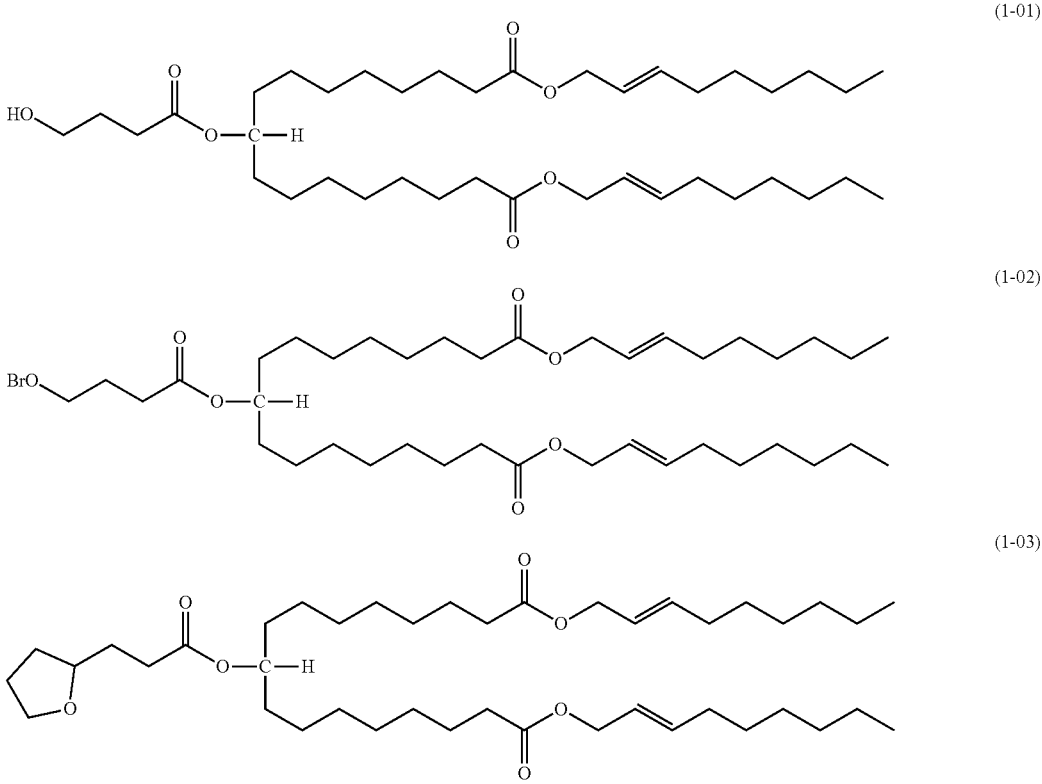

(1-04)
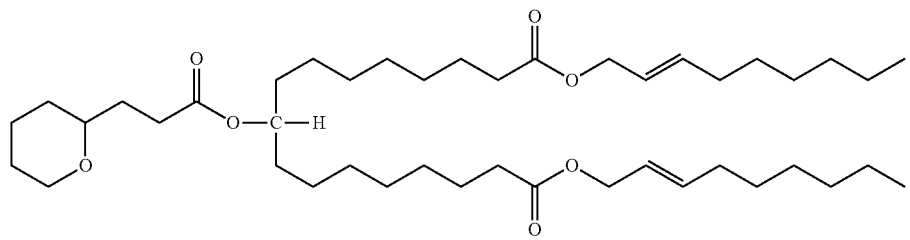
(1-05)
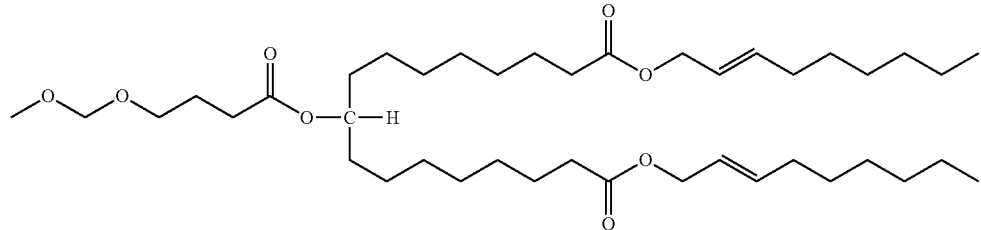
(1-06)
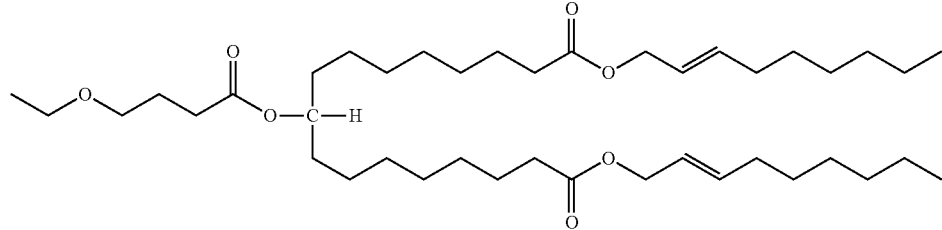
(1-07)
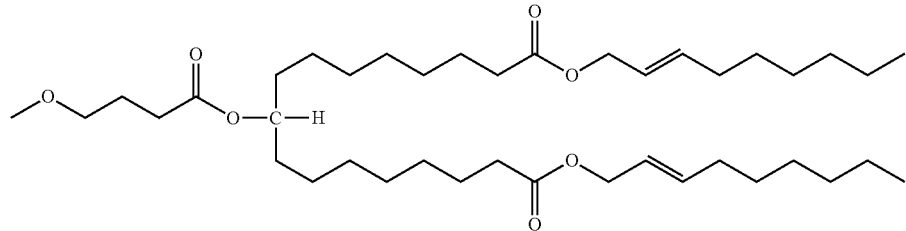
(1-08)
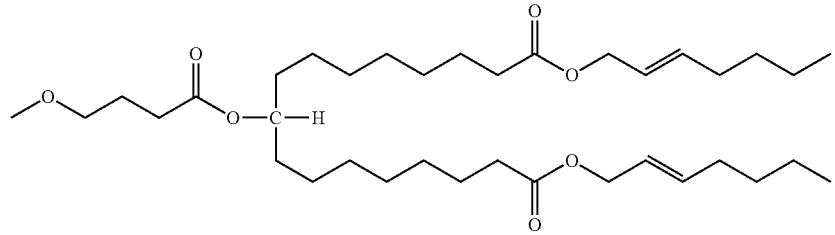
(1-09)
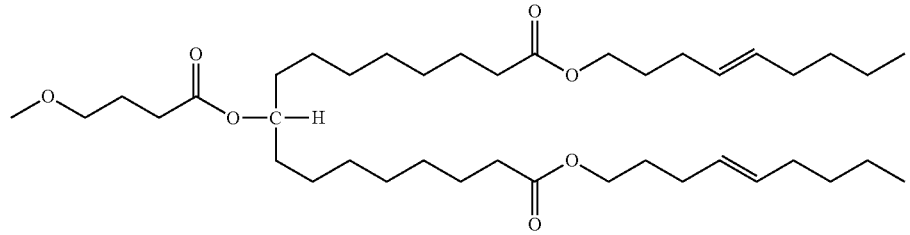

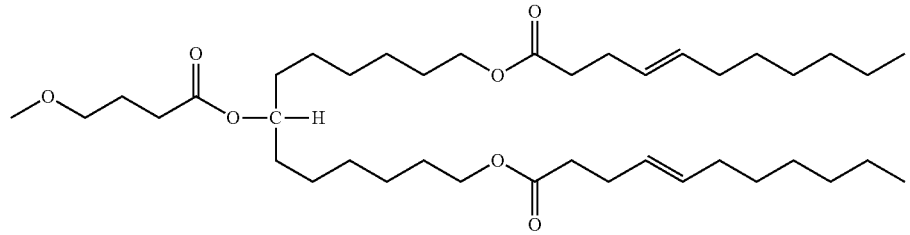
(1-10)
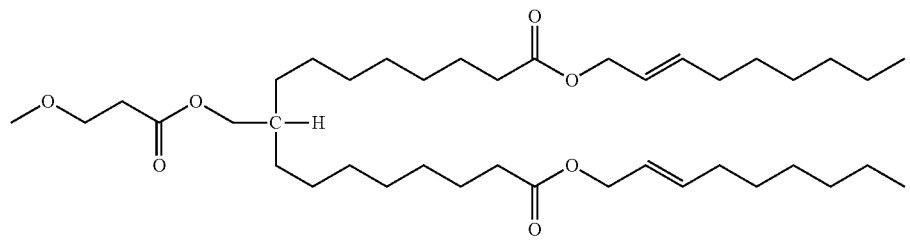
(1-11)
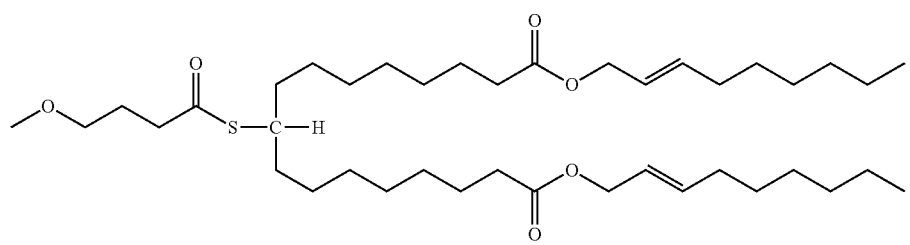
(1-12)
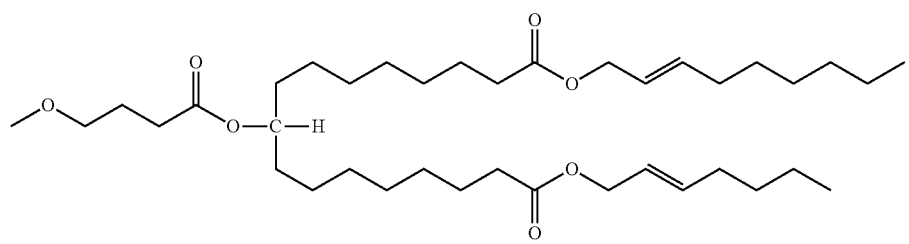
(1-14)
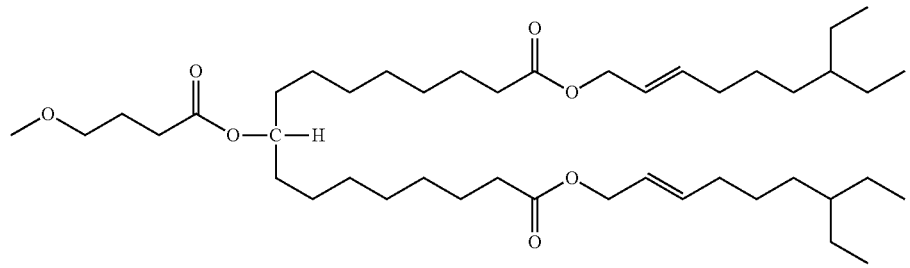
(1-15)
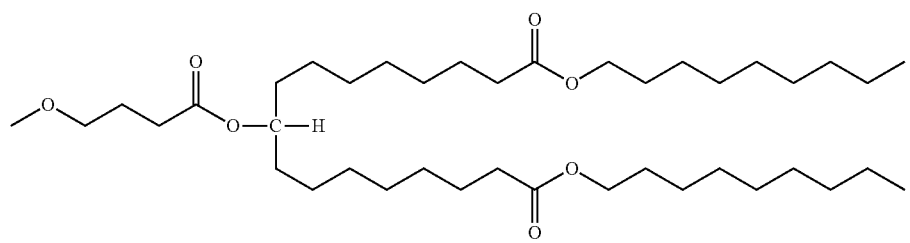
(1-16)

-continued (1-17)
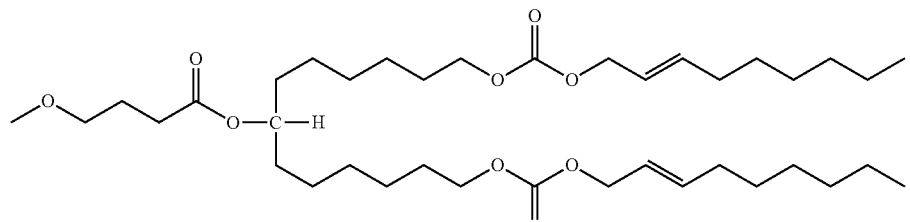

(1-18)
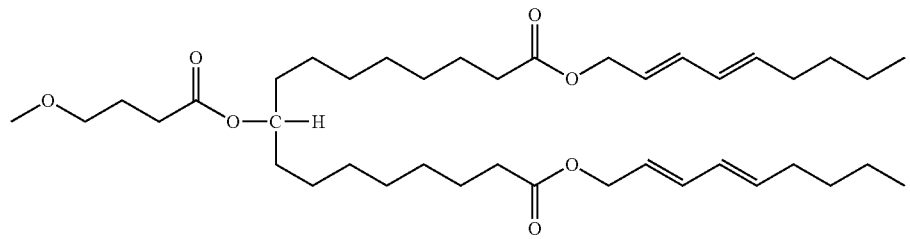

(1-19)
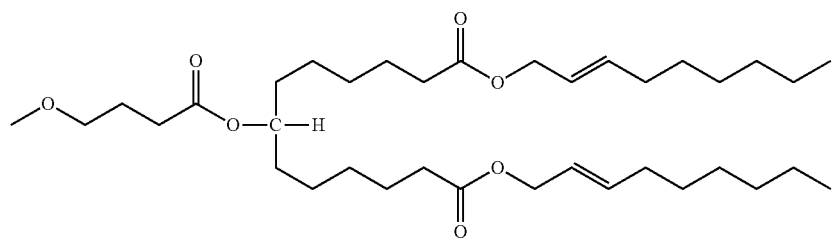

(1-20)
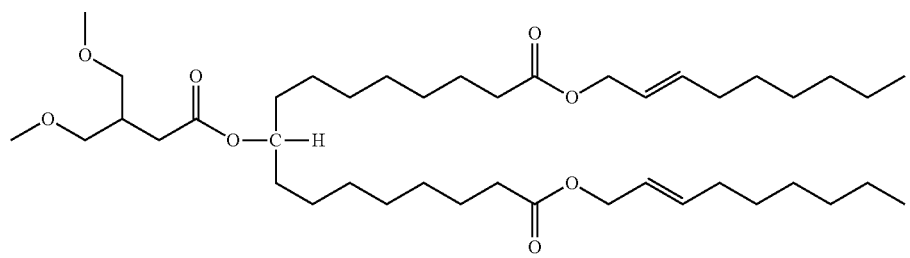

28. A lipid particle comprising the compound according to claim 20.

29. The lipid particle according to claim 28, further comprising a membrane-forming lipid and an aggregation-reducing lipid.

30. The lipid particle according to claim 29, wherein the membrane-forming lipid is selected from the group consisting of
1,2-dioleoyl-sn-glycero-3-phosphoethanol amine (DOPE),
1,2-stearoyl-sn-glycero-3-phosphoethanol amine (DSPE),
1,2-dipalmitoyl-sn-glycero-3-phosphatidylcholine (DPPC),
1-palmitoyl-2-oleoyl-sn-glycero-3-phosphatidylcholine (POPC),
1,2-di-O-octadecyl-3-trimethylammonium propane (DOTMA),
1,2-dioleoyl-3-dimethylammonium propane (DODAP),
1,2-dimyristoyl-3-di methylammonium propane (14:0 DAP),
1,2-dipalmitoyl-3-dimethylammonium propane (16:0 DAP),
1,2-distearoyl-3-dimethylammonium propane (18:0 DAP),
N-(4-carboxybenzyl)-N,N-dimethyl-2,3-bis(oleoyloxy) propane (DOBAQ),
1,2-dioleoyl-3-trimethylammonium propane (DOTAP),
1,2-dioleoyl-sn-glycero-3-phosphochlorine (DOPC),
1,2-dilinoleoyl-sn-glycero-3-phosphochlorine (DLPC),
1,2-dioleoyl-sn-glycero-3-phospho-L-serine (DOPS), cholesterol, and the like; and
wherein the aggregation-reducing lipid is a polyethylene glycol (PEG)-modified lipid.

31. The lipid particle according to claim 28, further comprising an active agent.

32. The lipid particle according to claim 31, wherein the active agent is a nucleic acid selected from the group consisting of plasmids, oligonucleotides, polynucleotides, siRNAs, micro RNAs, DNAs, aptamers, and ribozymes.

33. The lipid particle according to claim 32, further comprising a compound that binds to a nucleic acid.

34. The lipid particle according to claim 33, wherein the compound that binds to a nucleic acid is a basic protein or a basic peptide.

35. The lipid particle according to claim 33, wherein the compound that binds to a nucleic acid is a protamine or a histone.

36. The lipid particle according to claim 33, further comprising a compound that regulates the expression of a nucleic acid in a cell.

37. A lipid particle comprising the compound which is represented by the following formula (1):

wherein,
  Q is a non-cationic aliphatic group that does not contain nitrogen but contains oxy;
  L is a single bond or an aliphatic group containing no nitrogen;
  Rs are $C_{12}$-$C_{24}$ aliphatic groups, the same or different; and at least one R contains, in the main chain or side chain thereof, a linking group $L^R$ selected from the group consisting of —C(=O)—O—, —O—C(=O)—, —O—C(=O)—O—, —S—C(=O)—, —C(=O)—S—, —C(=O)—NH—, and —NH—C(=O)—,
a membrane-forming lipid, and
an aggregation-reducing lipid.

38. The lipid particle according to claim 37, wherein the membrane-forming lipid is selected from the group consisting of
  1,2-dioleoyl-sn-glycero-3-phosphoethanol amine (DOPE),
  1,2-stearoyl-sn-glycero-3-phosphoethanol amine (DSPE),
  1,2-dipalmitoyl-sn-glycero-3-phosphatidylcholine (DPPC),
  1-palmitoyl-2-oleoyl-sn-glycero-3-phosphatidylcholine (POPC),
  1,2-di-O-octadecyl-3-trimethylammonium propane (DOTMA),
  1,2-dioleoyl-3-dimethylammonium propane (DODAP),
  1,2-dimyristoyl-3-di methylammonium propane (14:0 DAP),
  1,2-dipalmitoyl-3-dimethylammonium propane (16:0 DAP),
  1,2-distearoyl-3-dimethylammonium propane (18:0 DAP),
  N-(4-carboxybenzyl)-N,N-dimethyl-2,3-bis(oleoyloxy) propane (DOBAQ),
  1,2-dioleoyl-3-trimethylammonium propane (DOTAP),
  1,2-dioleoyl-sn-glycero-3-phosphochlorine (DOPC),
  1,2-dilinoleoyl-sn-glycero-3-phosphochlorine (DLPC),
  1,2-dioleoyl-sn-glycero-3-phospho-L-serine (DOPS), cholesterol, and the like; and
  wherein the aggregation-reducing lipid is a polyethylene glycol (PEG)-modified lipid.

39. The lipid particle according to claim 37, further comprising an active agent.

40. The lipid particle according to claim 39, wherein the active agent is a nucleic acid selected from the group consisting of plasmids, oligonucleotides, polynucleotides, siRNAs, micro RNAs, DNAs, aptamers, and ribozymes.

41. The lipid particle according to claim 40, further comprising a compound that binds to a nucleic acid.

42. The lipid particle according to claim 41, wherein the compound that binds to a nucleic acid is a basic protein or a basic peptide.

43. The lipid particle according to claim 41, wherein the compound that binds to a nucleic acid is a protamine or a histone.

44. The lipid particle according to claim 41, further comprising a compound that regulates the expression of a nucleic acid in a cell.

45. A composition comprising the lipid particle according to claim 28 and a carrier.

46. A kit comprising the lipid particle according to claim 28 and a composition containing an incorporation agent for incorporating the lipid particle into a cell.

47. A composition comprising the lipid particle according to claim 37 and a carrier.

48. A kit comprising the lipid particle according to claim 37 and a composition containing an incorporation agent for incorporating the lipid particle into a cell.

* * * * *